United States Patent
Moore et al.

(10) Patent No.: US 11,565,996 B2
(45) Date of Patent: Jan. 31, 2023

(54) COMPOUNDS FOR USE AS INHIBITORS OF ALTERNATIVE OXIDASE OR CYTOCHROME BC1 COMPLEX

(71) Applicant: AlternOx Scientific Limited, Brighton (GB)

(72) Inventors: Anthony Lennox Moore, Brighton (GB); Mary Susan Albury, Brighton (GB); Luke Edward Young, Brighton (GB); Catherine Elliott, Brighton (GB)

(73) Assignee: AlternOx Scientific Limited, Brighton (GB)

( * ) Notice: Subject to any disclaimer, the term of this patent is extended or adjusted under 35 U.S.C. 154(b) by 217 days.

(21) Appl. No.: 17/060,013

(22) Filed: Sep. 30, 2020

(65) Prior Publication Data

US 2021/0032198 A1 Feb. 4, 2021

Related U.S. Application Data

(62) Division of application No. 14/397,164, filed as application No. PCT/GB2013/051030 on Apr. 24, 2013.

(30) Foreign Application Priority Data

Apr. 25, 2012 (GB) .................................... 1207213
Aug. 22, 2012 (GB) .................................... 1214938

(51) Int. Cl.

| | | |
|---|---|---|
| C07C 255/53 | (2006.01) | |
| C07C 235/60 | (2006.01) | |
| A61K 31/11 | (2006.01) | |
| C07C 39/373 | (2006.01) | |
| C07C 47/565 | (2006.01) | |
| C07C 49/835 | (2006.01) | |
| A01N 49/00 | (2006.01) | |
| C07C 69/63 | (2006.01) | |
| C07C 65/28 | (2006.01) | |
| C07C 69/84 | (2006.01) | |
| C07C 69/18 | (2006.01) | |
| C07C 69/157 | (2006.01) | |
| C07C 39/24 | (2006.01) | |
| A01N 31/16 | (2006.01) | |
| A01N 35/04 | (2006.01) | |
| A01N 37/24 | (2006.01) | |
| A01N 37/40 | (2006.01) | |
| A01N 37/44 | (2006.01) | |
| C07C 43/178 | (2006.01) | |
| A01N 63/50 | (2020.01) | |
| A01N 37/02 | (2006.01) | |
| A01N 37/34 | (2006.01) | |
| A61K 31/055 | (2006.01) | |
| A61K 31/085 | (2006.01) | |
| A61K 31/12 | (2006.01) | |
| A61K 31/166 | (2006.01) | |
| A61K 31/222 | (2006.01) | |

(Continued)

(52) U.S. Cl.
CPC ............ *C07C 255/53* (2013.01); *A01N 31/16* (2013.01); *A01N 35/04* (2013.01); *A01N 37/02* (2013.01); *A01N 37/24* (2013.01); *A01N 37/34* (2013.01); *A01N 37/40* (2013.01); *A01N 37/44* (2013.01); *A01N 37/44* (2013.01); *A01N 49/00* (2013.01); *A01N 63/50* (2020.01); *A61K 31/055* (2013.01); *A61K 31/085* (2013.01); *A61K 31/11* (2013.01); *A61K 31/12* (2013.01); *A61K 31/166* (2013.01); *A61K 31/222* (2013.01); *A61K 31/277* (2013.01); *C07C 39/245* (2013.01); *C07C 39/373* (2013.01); *C07C 43/1787* (2013.01); *C07C 43/23* (2013.01); *C07C 47/565* (2013.01); *C07C 49/835* (2013.01); *C07C 65/28* (2013.01); *C07C 69/157* (2013.01); *C07C 69/18* (2013.01); *C07C 69/21* (2013.01); *C07C 69/63* (2013.01); *C07C 69/84* (2013.01); *C07C 235/60* (2013.01); *Y02A 50/30* (2018.01)

(58) Field of Classification Search
CPC ... C07C 255/53; C07C 39/245; C07C 39/373; C07C 43/1787; C07C 43/23; C07C 47/565; C07C 49/835; C07C 65/28; C07C 69/157; C07C 69/18; C07C 69/21; C07C 69/63; C07C 69/84; C07C 235/60; A01N 63/50; A01N 31/16; A01N 35/04; A01N 37/02; A01N 37/24; A01N 37/34; A01N 37/40; A01N 37/44; A01N 49/00; A61K 31/055; A61K 31/085; A61K 31/11; A61K 31/12; A61K 31/166; A61K 31/222; A61K 31/277; Y02A 50/30
See application file for complete search history.

(56) References Cited

U.S. PATENT DOCUMENTS

| | | |
|---|---|---|
| 3,546,073 A | 12/1970 | Evans et al. |
| 4,225,619 A | 9/1980 | Brickl et al. |
| 10,851,047 B2 | 12/2020 | Moore et al. |

FOREIGN PATENT DOCUMENTS

| | | |
|---|---|---|
| EP | 1681280 A1 | 7/2006 |
| JP | 2006-122010 A | 9/1994 |

(Continued)

OTHER PUBLICATIONS

"Abstracts Presented at the Meeting of the Kanto Division, Atsugi, Sep. 13-14, 2007" Japanese Journal of Phytopathology, 74(1):33-47, (2008). [Author Unknown].

(Continued)

*Primary Examiner* — James D. Anderson
*Assistant Examiner* — William Y Lee
(74) *Attorney, Agent, or Firm* — Alston & Bird LLP

(57) ABSTRACT

The invention provides compounds for use in inhibiting a microbial alternative oxidase (AOX) and/or cytochrome $bc_1$ complex. The invention extends to the use of such inhibitors in agrochemicals and in pharmaceuticals, for treating microbial infections, including fungal infections.

13 Claims, 9 Drawing Sheets

Specification includes a Sequence Listing.

(51) Int. Cl.
    *A61K 31/277* (2006.01)
    *C07C 43/23* (2006.01)
    *C07C 69/21* (2006.01)

(56) References Cited

FOREIGN PATENT DOCUMENTS

| JP | H06245778 A | 9/1994 |
|---|---|---|
| WO | WO 12/060387 A1 | 5/2012 |
| WO | WO 13/160670 A1 | 10/2013 |

OTHER PUBLICATIONS

Berry et al., "Ascochlorin is a novel, specific inhibitor of the mitochondrial cytochrome $bc_1$ complex," Biochimica et Biophysica Acta, 1797(3):360-370, (2010).

Guttierrez et al., "Bioactive metabolites from the fungus Nectria galligena, the main apple canker agent in Chile," J. Agric. Food Chem., 53(20):7701-7708, (2005).

Haga et al., "A short and efficient total synthesis of (±)-ascofuranone," Chem. Lett., 39(6):622-623, (2010).

Hayakawa et al., "The Ilicicolins, Antibiotics from Cylindrocladium Ilicicola," The Journal of Antibiotics, 24(9):653-654, (1971).

Ishii, et al., "Characterisation of QoI-resistant field isolates of Botrytis cinerea from citrus and strawberry," Pest Manag Sci, 65: 916-922, (2009).

JP Application No. 2017-111886, Office Action dated Jul. 3, 2018.

Krohn et al., "Biologically active metabolites from Fungi 14 3-Chloro-4-Hydroxy-5-(3,7,11-Trimethyldodeca-2,6,10-Trienyl)Benzamide, a New Antibacterial Agent from a Soil Fungus," Natural Product Letters, 15(1):09-12, (2001).

Mogi et al., "Antibiotics LL-Z1272 identified as novel inhibitors discriminating bacterial and mitochondria quinol oxidases," Biochimica et Biophysica Acta, 1787(2):129-133, (2009).

Saimoto et al., "A general approach for the synthesis of phenolic natural products. Facile syntheses of grifolin and colletochlorins B and D," Bull. Chem. Soc. Jpn., 67(4):1178-1185, (1994).

Saimoto et al., "Pharmacophore identification of ascofuranone, potent inhibitor of cyanide-insensitive alternative oxidase of *Trypanosoma brucei*," Journal of Biochemistry, 153(3):267-273, (2012).

Takahashi et al., "Differentiation induction of human promyelocytic leukemia cells with colletochlorin B and its analogues," Chem. Pharm. Bull., 36(1):452-455, (1988).

Tamura et al., "Mode of Action of Strobilurin Fungicides," Japanese Journal of Pesticide Science, 24(2):189-196, (1999).

UK Application No. GB 1207213.8, Search Report, dated Aug. 24, 2012.

UK Application No. GB 1214938.1, Search Report, dated Nov. 30, 2012.

U.S. Appl. No. 15/113,046 Final Office Action dated Dec. 15, 2017.

U.S. Appl. No. 15/113,046 Non-Final Office Action dated Jul. 27, 2018.

U.S. Appl. No. 15/113,046 Non-Final Office Action dated Jul. 28, 2017.

U.S. Appl. No. 15/113,046 Notice of Allowance dated Feb. 6, 2019.

WIPO Application No. PCT/GB2013/051030, International Preliminary Report on Patentability, dated Oct. 28, 2014.

WIPO Application No. PCT/GB2013/051030, International Search Report and Written Opinion of the International Searching Authority, dated Aug. 8, 2013.

Fig. 4C

SEQUENCE LISTING

<160> NUMBER OF SEQ ID NOS: 14

<210> SEQ ID NO 1
<211> LENGTH: 1775
<212> TYPE: DNA
<213> ORGANISM: Ch

<400> SEQUENCE: 1

```
tttatatatc cgatgtttgg tgacagcatt cttggtgcat gaaaagttac tcccggcggc      60
gaggaaccgg tgacttggga aagggagcg tttgttaatt gaaggactgg tacatggata     120
cctgcgtact tcatgcggtc ctttctcgtg gtggtaggcc tgcatttagg tttcttttgat    180
gtttgacgcc gcagttacac aggctgaggc tgacttggat ttcgtgtgtc ccgataagac     240
atcgtgaacg agttatttcc atcccttctt ttcttgttct cttttagttt gcttagaaga     300
cgttgccggc tttttttctt gactgaggtt gctcgggctt ttattcattc acctcttctt    360
agagttaccc gttgcttgcc gtgtttcttt gctagtggca attgaaatac aacacctacc    420
tactgtacct tcacacacct acaaaccttt ttcttatttc gtcaaaataa caggattctg     480
attgagacca ctatgtatgt ggcaagagta tccacgaggg tacagttctc caaacagact    540
gcttcgcatc tttccaaggt cgtagcagcc aacttttcac aatcatgttc tggctccctc     600
catcgcgttg tcttggtgc gagtccagta cttcatactt cacaatctca tcgtgagttc      660
tctacgacgc cccgagcagc gttgagagat ttcttccctc agaaggaaac ggaactgatc     720
cggaaaacca aaccagcatg gaacatccc gacttcagct acgaagacat gaaaaccaag     780
gtcttctatg cccaccgcga accagccgat ttctcagatc gtgtcgcatt atggatggtt     840
cgccttttaa gatggggaac cgacctagca acgggctaca aacacgatgt agaagtgcca     900
aagaaaatcg gtgatgccaa tgccgttgca gagacgaagc catatggtat gagtgagcga     960
aaatggttga ttcgaattat attttttggaa tctgttgcgg gtgtgccagg gatggttgcg    1020
gctatgttga ggcatttgca ttcgatgagg aggttgaaga gggataatgg atggattgag    1080
acgcttttgg aggagagtca gaatgagagg atgcatctcc tcaccttcct caaaatggcc    1140
gaaccaggct ggtcatgaa attcatgctc ctgggcgccc aaggcgtctt cttcaacagc     1200
atgttcatct cctacctcat ctccccacga acctgccacc gcttcgtcgg ctacctcgaa    1260
gaagaagccg tcttcacgta cacgctcgcc atccaagacc tggaagcggg caagctgccc    1320
caatggacgc acccggactt ccgcgtccca gacatcgccg tcgattactg aagatgccc     1380
gaggacaaac gcaccatgag ggatctcatg ctctatgtga gcgcgatga ggcgaaacat    1440
cgtgaggtta atcatacccct gggggaatctg gatcaggatg aggatccgaa tccgtttgtt   1500
tccgagtata aggatgtggg gaggccgcat cctgggaagg ggattgagca tgtgcagccg    1560
attgggtggg agaggaagga tgttatttga gagttggagc gaagtctttt gctctttctct   1620
tgatcgcgat cgatggctct cgacgactag atgagggact tgaagtctta aactgcgacc    1680
aggactgcat agagattact acagagaggc gttttgaggt ttttggcgtt ggtttatagg    1740
tgtgcaagat gggttcgggc gtttgttctg ctttt                                1775
```

<210> SEQ ID NO 2
<211> LENGTH: 325
<212> TYPE: PRT
<213> ORGANISM: Arabidopsis thaliana

<400> SEQUENCE: 2

```
Met Met Met Ser Arg Arg Tyr Gly Ala Lys Leu Met Glu Thr Ala Val
1               5                  10                  15

Thr His Ser His Leu Leu Asn Pro Arg Val Pro Leu Val Thr Glu Asn
            20                  25                  30

Ile Arg Val Pro Ala Met Gly Val Val Arg Val Phe Ser Lys Met Thr
        35                  40                  45
```

```
Phe Glu Lys Lys Lys Thr Thr Glu Glu Lys Gly Ser Ser Gly Gly Lys
 50                  55                  60

Ala Asp Gln Gly Asn Lys Gly Glu Gln Leu Ile Val Ser Tyr Trp Gly
 65                  70                  75                  80

Val Lys Pro Met Lys Ile Thr Lys Glu Asp Gly Thr Glu Trp Lys Trp
                 85                  90                  95

Ser Cys Phe Arg Pro Trp Glu Thr Tyr Lys Ser Asp Leu Thr Ile Asp
                100                 105                 110

Leu Lys Lys His His Val Pro Ser Thr Leu Pro Asp Lys Leu Ala Tyr
            115                 120                 125

Trp Thr Val Lys Ser Leu Arg Trp Pro Thr Asp Leu Phe Phe Gln Arg
130                 135                 140

Arg Tyr Gly Cys Arg Ala Met Met Leu Glu Thr Val Ala Ala Val Pro
145                 150                 155                 160

Gly Met Val Gly Gly Met Leu Val His Cys Lys Ser Leu Arg Arg Phe
                165                 170                 175

Glu Gln Ser Gly Gly Trp Ile Lys Ala Leu Leu Glu Glu Ala Glu Asn
                180                 185                 190

Glu Arg Met His Leu Met Thr Phe Met Glu Val Ala Lys Pro Asn Trp
            195                 200                 205

Tyr Glu Arg Ala Leu Val Ile Ala Val Gln Gly Ile Phe Phe Asn Ala
210                 215                 220

Tyr Phe Leu Gly Tyr Leu Ile Ser Pro Lys Phe Ala His Arg Met Val
225                 230                 235                 240

Gly Tyr Leu Glu Glu Glu Ala Ile His Ser Tyr Thr Glu Phe Leu Lys
                245                 250                 255

Glu Leu Asp Asn Gly Asn Ile Glu Asn Val Pro Ala Pro Ala Ile Ala
                260                 265                 270

Ile Asp Tyr Trp Arg Leu Glu Ala Asp Ala Thr Leu Arg Asp Val Val
            275                 280                 285

Met Val Val Arg Ala Asp Glu Ala His His Arg Asp Val Asn His Tyr
                290                 295                 300

Ala Ser Asp Ile His Tyr Gln Gly Arg Glu Leu Lys Glu Ala Pro Ala
305                 310                 315                 320

Pro Ile Gly Tyr His
                325

<210> SEQ ID NO 3
<211> LENGTH: 321
<212> TYPE: PRT
<213> ORGANISM: Glycine max

<400> SEQUENCE: 3

Met Met Met Met Met Ser Arg Ser Gly Ala Asn Arg Val Ala Asn Thr
  1               5                  10                  15

Ala Met Phe Val Ala Lys Gly Leu Ser Gly Glu Val Gly Gly Leu Arg
                 20                  25                  30

Ala Leu Tyr Gly Gly Gly Val Arg Ser Glu Ser Thr Leu Ala Leu Ser
             35                  40                  45

Glu Lys Glu Lys Ile Glu Lys Lys Val Gly Leu Ser Ser Ala Gly Gly
         50                  55                  60

Asn Lys Glu Glu Lys Val Ile Val Ser Tyr Trp Gly Ile Gln Pro Ser
 65                  70                  75                  80

Lys Ile Thr Lys Lys Asp Gly Thr Glu Trp Lys Trp Asn Cys Phe Ser
                 85                  90                  95
```

-continued

```
Pro Trp Gly Thr Tyr Lys Ala Asp Leu Ser Ile Asp Leu Glu Lys His
                100                 105                 110

Met Pro Pro Thr Thr Phe Leu Asp Lys Met Ala Phe Trp Thr Val Lys
        115                 120                 125

Val Leu Arg Tyr Pro Thr Asp Val Phe Phe Gln Arg Arg Tyr Gly Cys
    130                 135                 140

Arg Ala Met Met Leu Glu Thr Val Ala Val Pro Gly Met Val Ala
145                 150                 155                 160

Gly Met Leu Leu His Cys Lys Ser Leu Arg Arg Phe Glu His Ser Gly
                165                 170                 175

Gly Trp Phe Lys Ala Leu Leu Glu Glu Ala Glu Asn Gly Arg Met His
            180                 185                 190

Leu Met Thr Phe Met Glu Val Ala Lys Pro Lys Trp Tyr Glu Arg Ala
        195                 200                 205

Leu Val Ile Thr Val Gln Gly Val Phe Phe Asn Ala Tyr Phe Leu Gly
    210                 215                 220

Tyr Leu Leu Ser Pro Lys Phe Ala His Arg Met Phe Gly Tyr Leu Glu
225                 230                 235                 240

Glu Glu Ala Ile His Ser Tyr Thr Glu Phe Leu Lys Glu Leu Asp Lys
                245                 250                 255

Gly Asn Ile Glu Asn Val Pro Ala Pro Ala Ile Ala Ile Asp Tyr Trp
            260                 265                 270

Gln Leu Pro Pro Gly Ser Thr Leu Arg Asp Val Val Met Val Val Arg
        275                 280                 285

Ala Asp Glu Ala His His Arg Asp Val Asn His Phe Ala Ser Asp Ile
    290                 295                 300

His Tyr Gln Gly Arg Glu Leu Arg Glu Ala Ala Ala Pro Ile Gly Tyr
305                 310                 315                 320

His

<210> SEQ ID NO 4
<211> LENGTH: 353
<212> TYPE: PRT
<213> ORGANISM: Nicotiana tabacum

<400> SEQUENCE: 4

Met Met Thr Arg Gly Ala Thr Arg Met Thr Arg Thr Val Leu Gly His
1               5                   10                  15

Met Gly Pro Arg Tyr Phe Ser Thr Ala Ile Phe Arg Asn Asp Ala Gly
                20                  25                  30

Thr Gly Val Met Ser Gly Ala Ala Val Phe Met His Gly Val Pro Ala
            35                  40                  45

Asn Pro Ser Glu Lys Ala Val Val Thr Trp Val Arg His Phe Pro Val
        50                  55                  60

Met Gly Ser Arg Ser Ala Met Ser Met Ala Leu Asn Asp Lys Gln His
65                  70                  75                  80

Asp Lys Lys Ala Glu Asn Gly Ser Ala Ala Ala Thr Gly Gly Gly Asp
                85                  90                  95

Gly Gly Asp Glu Lys Ser Val Val Ser Tyr Trp Gly Val Gln Pro Ser
                100                 105                 110

Lys Val Thr Lys Glu Asp Gly Thr Glu Trp Lys Trp Asn Cys Phe Arg
        115                 120                 125

Pro Trp Glu Thr Tyr Lys Ala Asp Leu Ser Ile Asp Leu Thr Lys His
    130                 135                 140
```

```
His Ala Pro Thr Thr Phe Leu Asp Lys Phe Ala Tyr Trp Thr Val Lys
145                 150                 155                 160

Ser Leu Arg Tyr Pro Thr Asp Ile Phe Phe Gln Arg Arg Tyr Gly Cys
                165                 170                 175

Arg Ala Met Met Leu Glu Thr Val Ala Val Pro Gly Met Val Gly
            180                 185                 190

Gly Met Leu Leu His Cys Lys Ser Leu Arg Arg Phe Glu Gln Ser Gly
            195                 200                 205

Gly Trp Ile Lys Thr Leu Leu Asp Glu Ala Glu Asn Glu Arg Met His
        210                 215                 220

Leu Met Thr Phe Met Glu Val Ala Lys Pro Asn Trp Tyr Glu Arg Ala
225                 230                 235                 240

Leu Val Phe Ala Val Gln Gly Val Phe Phe Asn Ala Tyr Phe Val Thr
                245                 250                 255

Tyr Leu Leu Ser Pro Lys Leu Ala His Arg Ile Val Gly Tyr Leu Glu
            260                 265                 270

Glu Glu Ala Ile His Ser Tyr Thr Glu Phe Leu Lys Glu Leu Asp Lys
            275                 280                 285

Gly Asn Ile Glu Asn Val Pro Ala Pro Ala Ile Ala Ile Asp Tyr Cys
290                 295                 300

Arg Leu Pro Lys Asp Ser Thr Leu Leu Asp Val Val Leu Val Val Arg
305                 310                 315                 320

Ala Asp Glu Ala His His Arg Asp Val Asn His Phe Ala Ser Asp Ile
                325                 330                 335

His Tyr Gln Gly Gln Gln Leu Lys Asp Ser Pro Ala Pro Ile Gly Tyr
            340                 345                 350

His

<210> SEQ ID NO 5
<211> LENGTH: 332
<212> TYPE: PRT
<213> ORGANISM: Oryza sativa

<400> SEQUENCE: 5

Met Ser Ser Arg Met Ala Gly Ser Ala Ile Leu Arg Val His Gly Gly
1               5                   10                  15

Val Arg Leu Phe Thr Ala Ser Ala Thr Ser Pro Ala Ala Ala Ala
            20                  25                  30

Ala Ala Ala Arg Pro Phe Leu Ala Gly Gly Glu Ala Val Pro Gly Val
            35                  40                  45

Trp Gly Leu Arg Leu Met Ser Thr Ser Ser Val Ala Ser Thr Glu Ala
50                  55                  60

Ala Ala Lys Ala Glu Ala Lys Lys Ala Asp Ala Glu Lys Glu Val Val
65                  70                  75                  80

Val Asn Ser Tyr Trp Gly Ile Glu Gln Ser Lys Lys Leu Val Arg Glu
                85                  90                  95

Asp Gly Thr Glu Trp Lys Trp Ser Cys Phe Arg Pro Trp Glu Thr Tyr
            100                 105                 110

Thr Ala Asp Thr Ser Ile Asp Leu Thr Lys His His Val Pro Lys Thr
            115                 120                 125

Leu Leu Asp Lys Ile Ala Tyr Trp Thr Val Lys Ser Leu Arg Phe Pro
        130                 135                 140

Thr Asp Ile Phe Phe Gln Arg Arg Tyr Gly Cys Arg Ala Met Met Leu
145                 150                 155                 160
```

```
Glu Thr Val Ala Ala Val Pro Gly Met Val Gly Gly Met Leu Leu His
                165                 170                 175

Leu Arg Ser Leu Arg Arg Phe Glu Gln Ser Gly Gly Trp Ile Arg Thr
            180                 185                 190

Leu Leu Glu Glu Ala Glu Asn Glu Arg Met His Leu Met Thr Phe Met
        195                 200                 205

Glu Val Ala Asn Pro Lys Trp Tyr Glu Arg Ala Leu Val Ile Thr Val
    210                 215                 220

Gln Gly Val Phe Phe Asn Ala Tyr Phe Leu Gly Tyr Leu Leu Ser Pro
225                 230                 235                 240

Lys Phe Ala His Arg Val Val Gly Tyr Leu Glu Glu Glu Ala Ile His
                245                 250                 255

Ser Tyr Thr Glu Phe Leu Lys Asp Leu Glu Ala Gly Lys Ile Asp Asn
            260                 265                 270

Val Pro Ala Pro Ala Ile Ala Ile Asp Tyr Trp Arg Leu Pro Ala Asn
        275                 280                 285

Ala Thr Leu Lys Asp Val Val Thr Val Val Arg Ala Asp Glu Ala His
    290                 295                 300

His Arg Asp Val Asn His Phe Ala Ser Asp Ile His Tyr Gln Gly Met
305                 310                 315                 320

Glu Leu Lys Gln Thr Pro Ala Pro Ile Gly Tyr His
                325                 330

<210> SEQ ID NO 6
<211> LENGTH: 349
<212> TYPE: PRT
<213> ORGANISM: Sauromatum guttatum

<400> SEQUENCE: 6

Met Met Ser Ser Arg Leu Val Gly Thr Ala Leu Cys Arg Gln Leu Ser
1               5                   10                  15

His Val Pro Val Pro Gln Tyr Leu Pro Ala Leu Arg Pro Thr Ala Asp
            20                  25                  30

Thr Ala Ser Ser Leu Leu His Gly Cys Ser Ala Ala Pro Ala Gln
        35                  40                  45

Arg Ala Gly Leu Trp Pro Pro Ser Trp Phe Ser Pro Pro Arg His Ala
    50                  55                  60

Ser Thr Leu Ser Ala Pro Ala Gln Asp Gly Gly Lys Glu Lys Ala Ala
65                  70                  75                  80

Gly Thr Ala Gly Lys Val Pro Pro Gly Glu Asp Gly Ala Glu Lys
                85                  90                  95

Glu Ala Val Val Ser Tyr Trp Ala Val Pro Pro Ser Lys Val Ser Lys
            100                 105                 110

Glu Asp Gly Ser Glu Trp Arg Trp Thr Cys Phe Arg Pro Trp Glu Thr
        115                 120                 125

Tyr Gln Ala Asp Leu Ser Ile Asp Leu His Lys His Val Pro Thr
    130                 135                 140

Thr Ile Leu Asp Lys Leu Ala Leu Arg Thr Val Lys Ala Leu Arg Trp
145                 150                 155                 160

Pro Thr Asp Ile Phe Phe Gln Arg Arg Tyr Ala Cys Arg Ala Met Met
                165                 170                 175

Leu Glu Thr Val Ala Ala Val Pro Gly Met Val Gly Gly Val Leu Leu
            180                 185                 190

His Leu Lys Ser Leu Arg Arg Phe Glu His Ser Gly Gly Trp Ile Arg
        195                 200                 205
```

```
Ala Leu Leu Glu Glu Ala Glu Asn Glu Arg Met His Leu Met Thr Phe
    210                 215                 220

Met Glu Val Ala Gln Pro Arg Trp Tyr Glu Arg Ala Leu Val Leu Ala
225                 230                 235                 240

Val Gln Gly Val Phe Phe Asn Ala Tyr Phe Leu Gly Tyr Leu Leu Ser
                245                 250                 255

Pro Lys Phe Ala His Arg Val Val Gly Tyr Leu Glu Glu Glu Ala Ile
                260                 265                 270

His Ser Tyr Thr Glu Phe Leu Lys Asp Ile Asp Ser Gly Ala Ile Gln
                275                 280                 285

Asp Cys Pro Ala Pro Ala Ile Ala Leu Asp Tyr Trp Arg Leu Pro Gln
    290                 295                 300

Gly Ser Thr Leu Arg Asp Val Val Thr Val Val Arg Ala Asp Glu Ala
305                 310                 315                 320

His His Arg Asp Val Asn His Phe Ala Ser Asp Val His Tyr Gln Asp
                325                 330                 335

Leu Glu Leu Lys Thr Thr Pro Ala Pro Leu Gly Tyr His
                340                 345

<210> SEQ ID NO 7
<211> LENGTH: 353
<212> TYPE: PRT
<213> ORGANISM: Catharanthus roseus

<400> SEQUENCE: 7

Met Met Ser Arg Gly Ala Thr Arg Ile Ser Arg Ser Leu Ile Cys Gln
1               5                   10                  15

Ile Ser Pro Arg Tyr Phe Ser Ser Ala Ala Val Arg Gly His Glu Pro
                20                  25                  30

Ser Leu Gly Ile Leu Thr Ser Gly Gly Thr Thr Thr Phe Leu His Gly
            35                  40                  45

Asn Pro Gly Asn Gly Ser Glu Arg Thr Ala Leu Thr Trp Ile Lys Leu
        50                  55                  60

Pro Met Met Arg Ala Arg Ser Ala Ser Thr Val Ala Thr Val Asp Gln
65                  70                  75                  80

Lys Asp Lys Asp Glu Lys Arg Glu Asp Lys Asn Gly Val Ala Asp Gly
                85                  90                  95

Glu Asn Gly Asn Lys Ala Val Val Ser Tyr Trp Gly Val Glu Ala Pro
                100                 105                 110

Lys Leu Thr Lys Glu Asp Gly Thr Val Trp Arg Trp Thr Cys Phe Arg
            115                 120                 125

Pro Trp Glu Thr Tyr Lys Pro Asp Thr Asp Ile Glu Leu Lys Lys His
130                 135                 140

His Val Pro Val Thr Leu Leu Asp Lys Val Ala Phe Phe Thr Val Lys
145                 150                 155                 160

Ala Leu Arg Trp Pro Thr Asp Leu Phe Phe Gln Arg Arg Tyr Gly Cys
                165                 170                 175

Arg Ala Met Met Leu Glu Thr Val Ala Ala Val Pro Gly Met Val Gly
            180                 185                 190

Gly Met Leu Leu His Cys Lys Ser Leu Arg Arg Phe Glu His Ser Gly
            195                 200                 205

Gly Trp Ile Lys Ala Leu Leu Glu Glu Ala Glu Asn Glu Arg Met His
        210                 215                 220

Leu Met Thr Phe Met Glu Val Ser Lys Pro Arg Trp Tyr Glu Arg Ala
225                 230                 235                 240
```

```
Leu Val Phe Ala Val Gln Gly Val Phe Asn Ala Tyr Phe Leu Thr
                245                 250                 255

Tyr Leu Ala Ser Pro Lys Leu Ala His Arg Ile Val Gly Tyr Leu Glu
            260                 265                 270

Glu Glu Ala Ile His Ser Tyr Ser Glu Phe Leu Asn Glu Leu Asp Lys
            275                 280                 285

Gly Asn Ile Glu Asn Val Pro Ala Pro Ala Ile Ala Ile Asp Tyr Trp
            290                 295                 300

Gln Met Pro Pro Asp Ser Thr Leu Arg Asp Val Met Val Val Arg
305                 310                 315                 320

Ala Asp Glu Ala Leu His Arg Asp Val Asn His Tyr Ala Ser Asp Ile
            325                 330                 335

His Tyr Lys Gly Leu Glu Leu Lys Glu Ala Ala Ala Pro Leu Asp Tyr
            340                 345                 350

His

<210> SEQ ID NO 8
<211> LENGTH: 274
<212> TYPE: PRT
<213> ORGANISM: Mangifera indica

<400> SEQUENCE: 8

Met Leu Ser Asn Ala Gly Gly Ala Glu Ala Gln Val Lys Glu Gln Lys
1               5                   10                  15

Glu Glu Lys Lys Asp Ala Met Val Ser Asn Tyr Trp Gly Ile Ser Arg
            20                  25                  30

Pro Lys Ile Thr Arg Glu Asp Gly Ser Glu Trp Pro Trp Asn Cys Phe
            35                  40                  45

Met Pro Trp Glu Thr Tyr Arg Ser Asp Leu Ser Ile Asp Leu Lys Lys
    50                  55                  60

His His Val Pro Arg Thr Phe Met Asp Lys Phe Ala Tyr Arg Thr Val
65                  70                  75                  80

Lys Ile Leu Arg Val Pro Thr Asp Ile Phe Phe Gln Arg Arg Tyr Gly
                85                  90                  95

Cys Arg Ala Met Met Leu Glu Thr Val Ala Ala Val Pro Gly Met Val
            100                 105                 110

Gly Gly Met Leu Leu His Leu Lys Ser Leu Arg Lys Leu Glu Gln Ser
            115                 120                 125

Gly Gly Trp Ile Lys Ala Leu Leu Glu Glu Ala Glu Asn Glu Arg Met
            130                 135                 140

His Leu Met Thr Met Val Glu Leu Val Gln Pro Lys Trp Tyr Glu Arg
145                 150                 155                 160

Leu Leu Val Leu Ala Val Gln Gly Val Phe Phe Asn Ser Phe Phe Val
                165                 170                 175

Leu Tyr Val Leu Ser Pro Lys Leu Ala His Arg Ile Val Gly Tyr Leu
            180                 185                 190

Glu Glu Glu Ala Ile His Ser Tyr Thr Glu Tyr Leu Lys Asp Ile Asp
            195                 200                 205

Ser Gly Ala Ile Lys Asn Ile Pro Ala Pro Ala Ile Ala Ile Asp Tyr
            210                 215                 220

Trp Arg Leu Pro Lys Asp Ala Thr Leu Lys Asp Val Ile Thr Val Val
225                 230                 235                 240

Arg Ala Asp Glu Ala His His Arg Asp Val Asn His Phe Ala Ser Asp
                245                 250                 255
```

```
Val Gln Val Gln Gly Lys Glu Leu Arg Asp Ala Pro Ala Pro Val Gly
            260                 265                 270
Tyr His
```

<210> SEQ ID NO 9
<211> LENGTH: 149
<212> TYPE: PRT
<213> ORGANISM: Zea mays

<400> SEQUENCE: 9

```
Ala Met Met Leu Glu Thr Val Ala Ala Val Pro Gly Met Val Gly Gly
1               5                   10                  15

Met Leu Leu His Leu Arg Ser Leu Arg Arg Phe Glu Gln Ser Gly Gly
            20                  25                  30

Trp Ile Arg Ala Leu Leu Glu Glu Ala Glu Asn Glu Arg Met His Leu
        35                  40                  45

Met Thr Phe Met Glu Val Ala Lys Pro Arg Trp Tyr Glu Arg Ala Leu
    50                  55                  60

Val Ile Thr Val Gln Gly Val Phe Phe Asn Ala Tyr Phe Leu Gly Tyr
65                  70                  75                  80

Leu Leu Ser Pro Lys Phe Ala His Arg Val Val Gly Tyr Leu Glu Glu
                85                  90                  95

Glu Ala Ile His Ser Tyr Thr Glu Tyr Leu Lys Asp Leu Glu Ala Gly
            100                 105                 110

Lys Ile Glu Lys Arg Pro Ala Pro Ala Ile Ala Ile Asp Tyr Trp Arg
        115                 120                 125

Leu Pro Ala Asn Ala Thr Leu Lys Asp Val Val Thr Val Arg Ala
    130                 135                 140

Asp Glu Ala His His
145
```

<210> SEQ ID NO 10
<211> LENGTH: 360
<212> TYPE: PRT
<213> ORGANISM: Chlamydomonas reinhardtii

<400> SEQUENCE: 10

```
Met Leu Gln Thr Ala Pro Met Leu Pro Gly Leu Gly Pro His Leu Val
1               5                   10                  15

Pro Gln Leu Gly Ala Leu Ala Ser Ala Ser Arg Leu Leu Gly Ser Ile
            20                  25                  30

Ala Ser Val Pro Pro Gln His Gly Gly Ala Gly Phe Gln Ala Val Arg
        35                  40                  45

Gly Phe Ala Thr Gly Ala Val Ser Thr Pro Ala Ala Ser Ser Pro Gly
    50                  55                  60

His Lys Pro Ala Ala Thr His Ala Pro Pro Thr Arg Leu Asp Leu Lys
65                  70                  75                  80

Pro Gly Ala Gly Ser Phe Ala Ala Gly Ala Val Ala Pro His Pro Gly
                85                  90                  95

Ile Asn Pro Ala Arg Met Ala Ala Asp Ser Ala Ser Ala Ala Ala Gly
            100                 105                 110

Ala Ser Gly Asp Ala Ala Leu Ala Glu Ser Tyr Met Ala His Pro Ala
        115                 120                 125

Tyr Ser Asp Glu Tyr Val Glu Ser Val Arg Pro Thr His Val Thr Pro
    130                 135                 140
```

-continued

```
Gln Lys Leu His Gln His Val Gly Leu Arg Thr Ile Gln Val Phe Arg
145                 150                 155                 160

Tyr Leu Phe Asp Lys Ala Thr Gly Tyr Thr Pro Thr Gly Ser Met Thr
                165                 170                 175

Glu Ala Gln Trp Leu Arg Arg Met Ile Phe Leu Glu Thr Val Ala Gly
            180                 185                 190

Cys Pro Gly Met Val Ala Gly Met Leu Arg His Leu Lys Ser Leu Arg
        195                 200                 205

Ser Met Ser Arg Asp Arg Gly Trp Ile His Thr Leu Leu Glu Glu Ala
    210                 215                 220

Glu Asn Glu Arg Met His Leu Ile Thr Phe Leu Gln Leu Arg Gln Pro
225                 230                 235                 240

Gly Pro Ala Phe Arg Ala Met Val Ile Leu Ala Gln Gly Val Phe Phe
                245                 250                 255

Asn Ala Tyr Phe Ile Ala Tyr Leu Leu Ser Pro Arg Thr Cys His Ala
                260                 265                 270

Phe Val Gly Phe Leu Glu Glu Glu Ala Val Lys Thr Tyr Thr His Ala
            275                 280                 285

Leu Val Glu Ile Asp Ala Gly Arg Leu Trp Lys Asp Thr Pro Ala Pro
290                 295                 300

Pro Val Ala Val Gln Tyr Trp Gly Leu Lys Pro Gly Ala Asn Met Arg
305                 310                 315                 320

Asp Leu Ile Leu Ala Val Arg Ala Asp Glu Ala Cys His Ala His Val
                325                 330                 335

Asn His Thr Leu Ser Gln Leu Asn Pro Ser Thr Asp Ala Asn Pro Phe
            340                 345                 350

Ala Thr Gly Ala Ser Gln Leu Pro
            355                 360

<210> SEQ ID NO 11
<211> LENGTH: 362
<212> TYPE: PRT
<213> ORGANISM: Neuropsora crassa

<400> SEQUENCE: 11

Met Asn Thr Pro Lys Val Asn Ile Leu His Ala Pro Gly Gln Ala Ala
1               5                   10                  15

Gln Leu Ser Arg Ala Leu Ile Ser Thr Cys His Thr Arg Pro Leu Leu
            20                  25                  30

Leu Ala Gly Ser Arg Val Ala Thr Ser Leu His Pro Thr Gln Thr Asn
        35                  40                  45

Leu Ser Ser Pro Ser Pro Arg Asn Phe Ser Thr Thr Ser Val Thr Arg
    50                  55                  60

Leu Lys Asp Phe Phe Pro Ala Lys Glu Thr Ala Tyr Ile Arg Gln Thr
65                  70                  75                  80

Pro Pro Ala Trp Pro His His Gly Trp Thr Glu Glu Glu Met Thr Ser
                85                  90                  95

Val Val Pro Glu His Arg Lys Pro Glu Thr Val Gly Asp Trp Leu Ala
            100                 105                 110

Trp Lys Leu Val Arg Ile Cys Arg Trp Ala Thr Asp Ile Ala Thr Gly
        115                 120                 125

Ile Arg Pro Glu Gln Gln Val Asp Lys His His Pro Thr Thr Ala Thr
    130                 135                 140
```

```
Ser Ala Asp Lys Pro Leu Thr Glu Ala Gln Trp Leu Val Arg Phe Ile
145                 150                 155                 160

Phe Leu Glu Ser Ile Ala Gly Val Pro Gly Met Val Ala Gly Met Leu
                165                 170                 175

Arg His Leu His Ser Leu Arg Arg Leu Lys Arg Asp Asn Gly Trp Ile
            180                 185                 190

Glu Thr Leu Leu Glu Glu Ser Tyr Asn Glu Arg Met His Leu Leu Thr
        195                 200                 205

Phe Met Lys Met Cys Glu Pro Gly Leu Leu Met Lys Thr Leu Ile Leu
    210                 215                 220

Gly Ala Gln Gly Val Phe Phe Asn Ala Met Phe Leu Ser Tyr Leu Ile
225                 230                 235                 240

Ser Pro Lys Ile Thr His Arg Phe Val Gly Tyr Leu Glu Glu Glu Ala
                245                 250                 255

Val His Thr Tyr Thr Arg Cys Ile Arg Glu Ile Glu Glu Gly His Leu
            260                 265                 270

Pro Lys Trp Ser Asp Glu Lys Phe Glu Ile Pro Glu Met Ala Val Arg
        275                 280                 285

Tyr Trp Arg Met Pro Glu Gly Lys Arg Thr Met Lys Asp Leu Ile His
    290                 295                 300

Tyr Ile Arg Ala Asp Glu Ala Val His Arg Gly Val Asn His Thr Leu
305                 310                 315                 320

Ser Asn Leu Asp Gln Lys Glu Asp Pro Asn Pro Phe Val Ser Asp Tyr
                325                 330                 335

Lys Glu Gly Glu Gly Gly Arg Arg Pro Val Asn Pro Ala Leu Lys Pro
            340                 345                 350

Thr Gly Phe Glu Arg Ala Glu Val Ile Gly
        355                 360

<210> SEQ ID NO 12
<211> LENGTH: 342
<212> TYPE: PRT
<213> ORGANISM: Hansenula anomola

<400> SEQUENCE: 12

Met Ile Lys Thr Tyr Gln Tyr Arg Ser Ile Leu Asn Ser Arg Asn Val
1               5                   10                  15

Gly Ile Arg Phe Leu Lys Thr Leu Ser Pro Ser Pro His Ser Lys Asp
            20                  25                  30

Pro Asn Ser Lys Ser Ile Phe Asp Ile Gly Thr Lys Leu Ile Val Asn
        35                  40                  45

Pro Pro Pro Gln Met Ala Asp Asn Gln Tyr Val Thr His Pro Leu Phe
    50                  55                  60

Pro His Pro Lys Tyr Ser Asp Glu Asp Cys Glu Ala Val His Phe Val
65                  70                  75                  80

His Arg Glu Pro Lys Thr Ile Gly Asp Lys Ile Ala Asp Arg Gly Val
                85                  90                  95

Lys Phe Cys Arg Ala Ser Phe Asp Phe Val Thr Gly Tyr Lys Lys Pro
            100                 105                 110

Lys Asp Val Asn Gly Met Leu Lys Ser Trp Glu Gly Thr Arg Tyr Glu
        115                 120                 125

Met Thr Glu Glu Lys Trp Leu Thr Arg Cys Ile Phe Leu Glu Ser Val
    130                 135                 140

Ala Gly Val Pro Gly Met Val Ala Ala Phe Ile Arg His Leu His Ser
145                 150                 155                 160
```

-continued

```
Leu Arg Leu Leu Lys Arg Asp Lys Ala Trp Ile Glu Thr Leu Leu Asp
                165                 170                 175

Glu Ala Tyr Asn Glu Arg Met His Leu Leu Thr Phe Ile Lys Ile Gly
            180                 185                 190

Asn Pro Ser Trp Phe Thr Arg Phe Ile Ile Tyr Met Gly Gln Gly Val
        195                 200                 205

Phe Ala Asn Leu Phe Phe Leu Val Tyr Leu Ile Lys Pro Arg Tyr Cys
    210                 215                 220

His Arg Phe Val Gly Tyr Leu Glu Glu Glu Ala Val Ser Thr Tyr Thr
225                 230                 235                 240

His Leu Ile Lys Asp Ile Asp Ser Lys Arg Leu Pro Lys Phe Asp Asp
                245                 250                 255

Val Asn Leu Pro Glu Ile Ser Trp Leu Tyr Trp Thr Asp Leu Asn Glu
            260                 265                 270

Lys Ser Thr Phe Arg Asp Leu Ile Gln Arg Ile Arg Ala Asp Glu Ser
        275                 280                 285

Lys His Arg Glu Val Asn His Thr Leu Ala Asn Leu Glu Gln Lys Lys
    290                 295                 300

Asp Arg Asn Pro Phe Ala Leu Lys Val Glu Asp Val Pro Lys Glu Gln
305                 310                 315                 320

Gln Pro Asp Glu Tyr Ser Leu Lys Thr Pro His Pro Glu Gly Trp Asn
                325                 330                 335

Arg Glu Gln Met Arg Leu
            340

<210> SEQ ID NO 13
<211> LENGTH: 329
<212> TYPE: PRT
<213> ORGANISM: Trypanosoma brucei

<400> SEQUENCE: 13

Met Phe Arg Asn His Ala Ser Arg Ile Thr Ala Ala Ala Ala Pro Trp
1               5                   10                  15

Val Leu Arg Thr Ala Cys Arg Gln Lys Ser Asp Ala Lys Thr Pro Val
            20                  25                  30

Trp Gly His Thr Gln Leu Asn Arg Leu Ser Phe Leu Glu Thr Val Pro
        35                  40                  45

Val Val Pro Leu Arg Val Ser Asp Glu Ser Ser Glu Asp Arg Pro Thr
    50                  55                  60

Trp Ser Leu Pro Asp Ile Glu Asn Val Ala Ile Thr His Lys Lys Pro
65                  70                  75                  80

Asn Gly Leu Val Asp Thr Leu Ala Tyr Arg Ser Val Arg Thr Cys Arg
                85                  90                  95

Trp Leu Phe Asp Thr Phe Ser Leu Tyr Arg Phe Gly Ser Ile Thr Glu
            100                 105                 110

Ser Lys Val Ile Ser Arg Cys Leu Phe Leu Glu Thr Val Ala Gly Val
        115                 120                 125

Pro Gly Met Val Gly Gly Met Leu Arg His Leu Ser Ser Leu Arg Tyr
    130                 135                 140

Met Thr Arg Asp Lys Gly Trp Ile Asn Thr Leu Leu Val Glu Ala Glu
145                 150                 155                 160
```

Asn Glu Arg Met His Leu Met Thr Phe Ile Glu Leu Arg Gln Pro Gly
                165                 170                 175

Leu Pro Leu Arg Val Ser Ile Ile Thr Gln Ala Ile Met Tyr Leu
            180                 185                 190

Phe Leu Leu Val Ala Tyr Val Ile Ser Pro Arg Phe Val His Arg Phe
            195                 200                 205

Val Gly Tyr Leu Glu Glu Ala Val Ile Thr Tyr Thr Gly Val Met
210                 215                 220

Arg Ala Ile Asp Glu Gly Arg Leu Arg Pro Thr Lys Asn Asp Val Pro
225                 230                 235                 240

Glu Val Ala Arg Val Tyr Trp Asn Leu Ser Lys Asn Ala Thr Phe Arg
                245                 250                 255

Asp Leu Ile Asn Val Ile Arg Ala Asp Glu Ala Glu His Arg Val Val
                260                 265                 270

Asn His Thr Phe Ala Asp Met His Glu Lys Arg Leu Gln Asn Ser Val
            275                 280                 285

Asn Pro Phe Val Val Leu Lys Lys Asn Pro Glu Glu Met Tyr Ser Asn
290                 295                 300

Gln Pro Ser Gly Lys Thr Arg Thr Asp Phe Gly Ser Glu Gly Ala Lys
305                 310                 315                 320

Thr Ala Ser Asn Val Asn Lys His Val
                325

<210> SEQ ID NO 14
<211> LENGTH: 155
<212> TYPE: PRT
<213> ORGANISM: Chlamydomonas

<400> SEQUENCE: 14

Gly Ser Pro Gly Leu Gln Ala Leu Leu Glu Glu Ala Glu Asn Glu Arg
1               5                   10                  15

Met His Leu Leu Thr Phe Leu Glu Met Arg Gln Pro Ser Trp Met Phe
                20                  25                  30

Arg Ala Ala Val Leu Leu Ala Gln Gly Ala Tyr Phe Asn Met Phe Phe
            35                  40                  45

Ile Ser Tyr Leu Ile Ser Pro Lys Phe Cys His Ala Val Val Gly Tyr
50                  55                  60

Leu Glu Glu Glu Ala Val Lys Thr Tyr Thr His Leu Leu His Asp Ile
65                  70                  75                  80

Asp Ala Gly His Val Trp Lys Asp Lys Pro Ala Pro Lys Thr Gly Ile
            85                  90                  95

Ala Tyr Trp Lys Leu Ser Pro Asp Ala Thr Met Arg Asp Leu Ile Leu
                100                 105                 110

Ala Val Arg Ala Asp Glu Ala Ser His Ser Leu Val Asn His Thr Leu
            115                 120                 125

Ser Glu Ile Pro Ser Asp Ala Pro Asn Pro Phe Ile Glu Pro Ala Lys
        130                 135                 140

Ala Asp Ala Phe Ser Lys Ala Glu Asn Lys Leu
145                 150                 155

COMPOUNDS FOR USE AS INHIBITORS OF ALTERNATIVE OXIDASE OR CYTOCHROME BC1 COMPLEX

CROSS REFERENCE TO RELATED APPLICATIONS

The present application is a divisional of U.S. Ser. No. 14/397,164 filed Oct. 24, 2014, which is a US national stage of PCT/GB2013/051030 filed Apr. 24, 2013, incorporated by reference in its entirety for all purposes, which claims the benefit of GB 1214938.1 filed Aug. 22, 2012 and GB 1207213.8 filed Apr. 25, 2012

REFERENCE TO SEQUENCE LISTING

This application includes an electronic sequence listing in a file named 4537523DIV_SEQLST.TXT, created on Sep. 30, 2020, and containing 37,903 bytes, which is hereby incorporated by reference.

The present invention relates to alternative oxidases (AOXs) and, in particular, to inhibitors of alternative oxidases. The invention also relates to inhibitors of the cytochrome bc1 complex. The invention is especially concerned with dual inhibitors of both AOXs and the cytochrome bc1 complex. The invention extends to the use of such inhibitors in agrochemicals and in pharmaceuticals, for treating microbial infections, including fungal infections, as well as to agrochemical and pharmaceutical compositions per se.

Fungicides have long been used to control crop losses. The most successful class of agricultural fungicides are a set of specific inhibitors which specifically target the mitochondrial respiratory chain. Mitochondria are the power-house of the cell and, hence, inhibition of the processes that result in an organism's energy conservation have a major impact on their capability to survive. Over the last decade, inhibitors known as strobilurins, which target the oxidation of ubiquinol, a pivotal respiratory chain component, have improved the standards of disease control in plants (see FIG. 1). Strobilurins inhibit fungal respiration and, hence, ATP synthesis by binding to the ubiquinol binding site of Complex III (the bc1 complex), which is essential for fungal respiration.

The strobilurins soon became one of the most important and successful agricultural fungicides accounting for over 20% of the global fungicide market. Since their introduction, this class of inhibitors has become essential to plant disease control programmes because of their wide-ranging efficacy against many agriculturally important fungal diseases. They have been registered in numerous countries for use on crops including cereals, turf grass, grapevine and numerous vegetables and ornamentals.

However, unfortunately, one of the apparent strengths of these systemic fungicides, namely their highly specific mode of action, is proving to be a significant weakness, since the rapid development of resistance to these fungicides and consequent control failure has become increasingly problematic.

In most cases, resistance was considered to be due to modification of the target site of the strobilurin, i.e. the apocytochrome b encoded by the mitochondrial genome. However, in recent years, an increasing amount of evidence suggests that resistance may be caused by other mechanisms, such as the expression of an alternative oxidase (AOX). The AOX is a mitochondrial terminal oxidase, which, when engaged, by-passes the Qo (quinone-outside) site, and increases resistance of the plasma membrane efflux transporters to the fungicide. Efflux transporters enable fungi to survive exposure to toxic compounds by preventing their accumulation to toxic concentrations within fungal cells. Although there is some experimental evidence for cytochrome b mutations and increased resistance of efflux transporters, the possibility that the cause of fungicide resistance in phytopathogenic fungi is due to the expression of the alternative oxidase (AOX) is increasing.

The AOX is a terminal mitochondrial respiratory chain complex that branches from the main respiratory chain at the level of ubiquinone and, hence, bypasses the bc1 complex and cytochrome c oxidase, as shown in FIG. 1. AOX is not only relevant to plant fungal pathogens, because it is also present in human parasites including trypanosomes, which is the cause of African sleeping sickness, and also *Cryptosporidium parvum* and *Blastocystis hominis*, which are intestinal parasites.

In plants and fungi, expression of AOX is induced under conditions of oxidative stress, for instance when the main respiratory pathway is inhibited. Currently available inhibitors of the AOX include salicylhydroxamic acids and octylgallates. However, neither of these two classes of inhibitors is either a potent or specific target of AOX in cells, and they are therefore unsuitable for agrochemical (i.e. crop) or pharmaceutical applications.

There is therefore a need to design more specific and potent inhibitors of AOX in order to produce improved fungicidal agents, for use in either agrochemicals or anti-parasitic pharmaceuticals.

The inventors have elucidated the molecular structure and catalytic mechanism of the alternative oxidase enzyme (AOX) in the plant, *Sauromatum guttatum*, and demonstrated how this information relates to the protein's physiological role. Clearly, such fundamental knowledge is of considerable industrial relevance, and has enabled the rational design of AOX inhibitor compounds, which can be used in phytopathogenic fungicides and anti-parasitic pharmaceuticals that are targeted at mitochondrial respiration.

Thus, according to a first aspect of the invention, there is provided an alternative oxidase (AOX) inhibitor of formula I:—

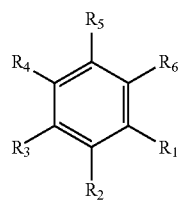

[Formula I]

wherein $R^1$ is selected from a nitrile group, an alkyl, alkenyl, amine group with 1 to 4 C-atoms that is optionally mono- or polysubstituted by F, O, $NH_2$ or CN, and in which one or more non-adjacent $CH_2$ groups are optionally replaced, in each case independently from one another, by —O—, —NH—, —CO—, —COO—, or —OCO—;

$R^2$ is hydrogen or a hydroxy or alkoxy group with 1 to 3 C atoms;

$R^3$ is a straight chain or branched alkyl or alkylene with 4 to 20 C atoms, that is optionally mono- or polysubstituted by a $C_1$ to $C_4$ alkyl group;

$R^4$ is hydrogen or a hydroxy or alkoxy group with 1 to 3 C atoms;

$R^5$ is a halogen group; and $R^6$ is H or a $C_1$ to $C_4$ alkyl group;

with the proviso that at least one of $R^2$ and $R^4$ is a hydroxy or alkoxy group with 1 to 3 C atoms.

Where any group is an alkyl group, it may be a $C_1$, $C_2$, $C_3$ or $C_4$ alkyl, for example a methyl, ethyl, propyl or butyl group. Optionally, the alkyl group may be substituted with one or more heteroatoms, for example nitrogen, oxygen, sulphur, phosphorous or a halogen.

$R^1$ may be a group selected from: CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$.

$R^2$ may be a short-chain alkyl, for example a methyl, ethyl or propyl group. However, preferably $R^2$ is a hydroxyl group.

$R^3$ may be a straight chain or branched alkyl or alkylene with 6 to 15 C atoms, 8 to 12 C atoms or 8 to m C atoms, that is optionally mono- or polysubstituted by a $C_1$ to $C_4$ alkyl group. For example, $R^3$ may be branched diene having 6 to 15 C atoms that is substituted with at least one, and preferably two, methyl groups.

$R^4$ may be a methyl, ethyl or propyl group. However, preferably $R^4$ is a hydroxyl group.

$R^5$ may be a chlorine, bromine, fluorine or iodine group. Preferably, $R^5$ is a chlorine group.

$R^6$ may be a methyl, ethyl or propyl group. However, preferably $R^4$ is a methyl group.

In one embodiment, the AOX inhibitor comprises a compound of formula I, wherein:—

$R^1$ is selected from CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$; and wherein $R^2$ is a hydroxyl group;

$R^3$ is a straight chain or branched alkyl or alkylene with 4 to 20 C atoms, that is optionally mono- or polysubstituted by a $C_1$ to $C_4$ alkyl group;

$R^4$ is a hydroxyl group;

$R^5$ is a chlorine atom; and $R^6$ is H or a $C_1$ to $C_4$ alkyl group.

In another embodiment, the AOX inhibitor comprises a compound of formula I, wherein:—

$R^1$ is selected from CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$; and wherein $R^2$ is a hydroxyl group;

$R^3$ is a straight chain or branched alkyl or alkylene with 6 to 15 C atoms, that is optionally mono- or polysubstituted by a $C_1$ to $C_2$ alkyl group;

$R^4$ is a hydroxyl group;

$R^5$ is a chlorine atom; and $R^6$ is H or a $C_1$ to $C_4$ alkyl group.

In one preferred embodiment, the AOX inhibitor comprises a compound of formula I, wherein:—

$R^1$ is selected from CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$; and wherein $R^2$ is a hydroxyl group;

$R^3$ is an alkylene chain having 8 to 10 C atoms, and is substituted with at least one methyl group, preferably two methyl groups;

$R^4$ is a hydroxyl group;

$R^5$ is a chlorine atom; and $R^6$ is a methyl group.

The inventors believe that the hydroxyl groups ($R^2$ and $R^4$) and the chlorine ($R^5$) and methyl ($R^6$) substituents on the benzene ring of the inhibitor compound may be important for high potency. In addition, the hydrophobic side chain, which may be a geranyl group, may also be important. However, the inventors believe that the aldehyde group present in a known compound, ascofuranone, may be problematic for anti-parasitic drug design for several reasons. Besides their ability to function as hydrogen bond acceptor and to undergo dipole-dipole interaction with AOX, aldehyde groups are chemically reactive enough to undergo reversible covalent modifications and would be generally unsuited to standard pharmaceutical formulations. Furthermore, aldehydes are prone to metabolic oxidation to the respective carboxylic acid with the concomitant non-specific binding to basic transport proteins. The inventors therefore believe that in some embodiments, it may be beneficial for there not to be an aldehyde group present.

Therefore, in some embodiments, $R^1$ is not a CHO group.

Preferably, the inhibitor of the first aspect is capable of inhibiting a microbial AOX. Preferably, the inhibitor is capable of inhibiting a fungal, bacterial or protist AOX. Examples of such micro-organisms which may be inhibited are provided herein. For example, the inhibitor may be capable of inhibiting an AOX from any of the organisms represented in FIGS. 4A-C. In particular, the inhibitor is capable of binding with any of the amino acid residues shown in the boxes in FIGS. 4A-C, as they represent conserved AOX residues which are believed to be involved in inhibitor binding.

Advantageously, the inhibitor can be synthesised using only a two-step process. For example, one embodiment of such a process is shown in FIG. 7.

As described in Example 6, the inventors have also surprisingly demonstrated that the compound of formula I is a specific inhibitor of the cytochrome $bc_1$ complex as well as being a potent inhibitor of AOX. Accordingly, the compound of formula I may be capable of inhibiting the cytochrome $bc_1$ complex. Advantageously, compounds of formula I can act as a specific and potent dual function fungicide, as not only do they inhibit the alternative oxidase (AOX), but also the cytochrome $bc_1$ complex. This makes the compound a very potent inhibitor of respiration even in the absence of an alternative oxidase.

Surprisingly, the data also suggest that the compound inhibits the cytochrome $bc_1$ complex at both the Qo (Quinone outside) and Qi (Quinone inside) binding sites of the Cytochrome $bc_1$ complex. Thus, the compound of formula I may inhibit the Qo and/or Qi binding site of the Cytochrome $bc_1$ complex. Preferably, however, the compound of formula I inhibits the Qo and Qi binding sites of cytochrome $bc_1$ complex. It will be appreciated that commercially available fungicides, such as azoxystrobin, inhibit only one site (Qo) within the bc1 complex. Accordingly, since compounds of the invention inhibit the cytochrome $bc_1$ complex at both the Qo and Qi binding sites, and also the AOX, such compounds act as highly potent and robust inhibitors.

In a second aspect, the invention provides a use of the compound of the first aspect, for inhibiting an alternative oxidase (AOX).

In a third aspect, there is provided use of a compound, for inhibiting a microbial alternative oxidase (AOX) and/or cytochrome $bc_1$ complex, wherein the compound is represented by formula I:—

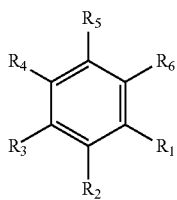

[Formula I]

wherein $R^1$ is selected from a nitrile group, an alkyl, alkenyl, amine group with 1 to 4 C-atoms that is optionally mono- or polysubstituted by F, O, $NH_2$ or CN, and in which one or more non-adjacent $CH_2$ groups are optionally replaced, in each case independently from one another, by —O—, —NH—, —CO—, —COO—, or —OCO—;
$R^2$ is hydrogen or a hydroxy or alkoxy group with 1 to 3 C atoms;
$R^3$ is a straight chain or branched alkyl or alkylene with 4 to 20 C atoms, that is optionally mono- or polysubstituted by a $C_1$ to $C_4$ alkyl group;
$R^4$ is hydrogen or a hydroxy or alkoxy group with 1 to 3 C atoms;
$R^5$ is a halogen group; and
$R^6$ is H or a $C_1$ to $C_4$ alkyl group;
with the proviso that at least one of $R^2$ and $R^4$ is a hydroxy or alkoxy group with 1 to 3 C atoms.

Accordingly, the compound that is used may be the inhibitor as defined herein. The use may be carried out in vitro or in vivo. The use may comprise inhibiting a microbial AOX, which may be a fungal, bacterial or protist AOX, as defined herein. The use may comprise inhibiting the cytochrome $bc_1$ complex, preferably the Qo and/or Qi binding site of the cytochrome $bc_1$ complex. The inventors believe that this is an important feature of the invention.

Hence, in a fourth aspect, the invention provides a use of a compound of formula I, for inhibiting the cytochrome $bc_1$ complex, wherein the compound of formula I is represented as:—

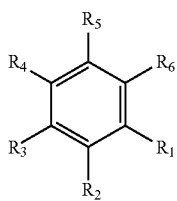

[Formula I]

wherein $R^1$ is selected from a nitrile group, an alkyl, alkenyl, amine group with 1 to 4 C-atoms that is optionally mono- or polysubstituted by F, O, $NH_2$ or CN, and in which one or more non-adjacent $CH_2$ groups are optionally replaced, in each case independently from one another, by —O—, —NH—, —CO—, —COO—, or —OCO—;
$R^2$ is hydrogen or a hydroxy or alkoxy group with 1 to 3 C atoms;
$R^3$ is a straight chain or branched alkyl or alkylene with 4 to 20 C atoms, that is optionally mono- or polysubstituted by a $C_1$ to $C_4$ alkyl group;
$R^4$ is hydrogen or a hydroxy or alkoxy group with 1 to 3 C atoms;
$R^5$ is a halogen group; and
$R^6$ is H or a $C_1$ to $C_4$ alkyl group;
with the proviso that at least one of $R^2$ and $R^4$ is a hydroxy or alkoxy group with 1 to 3 C atoms.

$R^1$ to $R^6$ may be defined as above. The use may comprise inhibiting the Qo and/or Qi binding site of the cytochrome $bc_1$ complex, and preferably both the Qo and Qi binding sites.

The inventors have found that the AOX inhibitors of the invention can be effectively used to treat infections of plant pathogens which comprise an AOX enzyme.

Thus, in a fifth aspect, there is provided use of the compound of formula I, which may be the alternative oxidase (AOX) inhibitor of the first aspect, as an agrochemical.

In a sixth aspect, there is provided use of the compound of formula I, which may be the alternative oxidase (AOX) inhibitor of the first aspect, for use as an agrochemical.

In a seventh aspect, there is provided an agrochemical composition comprising the compound of formula I, which may be alternative oxidase (AOX) inhibitor of the first aspect.

In an eighth aspect, there is provided use of the agrochemical composition of the seventh aspect, for treating an agrochemical disease or infection.

An agrochemical disease, which may be treated, may be caused by an organism selected from a group of organisms consisting of: *Chalara fraxinea*; *Septoria tritici*; *Gaeumannomyces graminis* var *titici*; *Magnaporthe grisea*; *Magnaporthe oryzae*; *Rhizoctonia solani*; *Botrytis cinerea*; *Fusicladium effusum* syn. *Cladosporium caryigenum* and *Fusicladosporium effusum*; *Carya illinoinensis*; *Podosphaera furca*; *Microdochium nivale*; *Microdochium majus*; *Septoria nodoum*; *Tapesia acuformis*; and *Metarhizium anisopliae*.

It will be appreciated that *Septoria tritici* and *Gaeumannomyces graminis* var *titici* are wheat pathogens (take-all); *Magnaporthe grisea* and *Magnaporthe oryzae* may cause rice blast and grey leaf spot of rye grass; *Rhizoctonia solani* may cause black scurf of potato, *Botrytis cinerea* may cause grey mold—a necrotrophic fungus that affects many plant species, although its most notable hosts are wine grapes; *Fusicladium effusum* (syn. *Cladosporium caryigenum* and *Fusicladosporium effusum* is known as the Pecan scab and is the most devastating disease of the commercial pecan; *Carya illinoinensis* is involved in the production in South Eastern United States; *Podosphaera furca* is the main causal agent of cucurbit powdery mildew in Spain and one of the most important limiting factors for cucurbit production worldwide; *Microdochium nivale* & *majus* may attack barley, durum wheat and soft wheat and is present in all areas of France; *Septoria nodoum* may cause leaf and glume blotch; and *Tapesia acuformis* may cause eyespot. In addition, there is growing agrochemical interest in *Metarhizium anisopliae* which is an entomopathogenic fungus as an alternative for the management of pest insects.

It will be appreciated that *Chalara fraxinea* causes Chalara ash dieback disease. The first DNA sequence for *Chalara fraxinea* has been published, as follows:—

[SEQ ID NO: 1]
TTTATATATCCGATGTTTGGTGACAGCATTCTTGGTGCATGAAAAGTTAC

TCCCGGCGGCGAGGAACCGGTGACTTGGGAGAAGGGAGCGTTTGTTAATT

GAAGGACTGGTACATGGATACCTGCGTACTTCATGCGGTCCTTTCTCGTG

GTGGTAGGCCTGCATTTAGGTTTCTTTGATGTTTGACGCCGCAGTTACAC

AGGCTGAGGCTGACTTGGATTTCGTGTGTCCCGATAAGACATCGTGAACG

```
                        -continued
AGTTATTTCCATCCCTTCTTTTCTTGTTCTCTTTTAGTTTGCTTAGAAGA

CGTTGCCGGCTTTTTTTCTTGACTGAGGTTGCTCGGGCTTTTATTCATTC

ACCTCTTCTTAGAGTTACCCGTTGCTTGCCGTGTTTCTTTGCTAGTGGCA

ATTGAAATACAACACCTACCTACTGTACCTTCACACACCTACAAACCTTT

TTCTTATTTCGTCAAAATAACAGGATTCTGATTGAGACCACTATGTATGT

GGCAAGAGTATCCACGAGGGTACAGTTCTCCAAACAGACTGCTTCGCATC

TTTCCAAGGTCGTAGCAGCCAACTTTTCACAATCATGTTCTGGCTCCCTC

CATCGCGTTGGTCTTGGTGCGAGTCCAGTACTTCATACTTCACAATCTCA

TCGTGAGTTCTCTACGACGCCCCGAGCAGCGTTGAGAGATTTCTTCCCTC

AGAAGGAAACGGAACTGATCCGGAAAACCAAACCAGCATGGGAACATCCC

GACTTCAGCTACGAAGACATGAAAACCAAGGTCTTCTATGCCCACCGCGA

ACCAGCCGATTTCTCAGATCGTGTCGCATTATGGATGGTTCGCCTTTTAA

GATGGGGAACCGACCTAGCAACGGGCTACAAACACGATGTAGAAGTGCCA

AAGAAAATCGGTGATGCCAATGCCGTTGCAGAGACGAAGCCATATGGTAT

GAGTGAGCGAAAATGGTTGATTCGAATTATATTTTTGGAATCTGTTGCGG

GTGTGCCAGGGATGGTTGCGGCTATGTTGAGGCATTTGCATTCGATGAGG

AGGTTGAAGAGGGATAATGGATGGATTGAGACGCTTTTGGAGGAGAGTCA

GAATGAGAGGATGCATCTCCTCACCTTCCTCAAAATGGCCGAACCAGGCT

GGTTCATGAAATTCATGCTCCTGGGCGCCCAAGGCGTCTTCTTCAACAGC

ATGTTCATCTCCTACCTCATCTCCCCACGAACCTGCCACCGCTTCGTCGG

CTACCTCGAAGAAGAAGCCGTCTTCACGTACACGCTCGCCATCCAAGACC

TGGAAGCGGGCAAGCTGCCCCAATGGACGCACCCGGACTTCCGCGTCCCA

GACATCGCCGTCGATTACTGGAAGATGCCCGAGGACAAACGCACCATGAG

GGATCTCATGCTCTATGTGAGAGCGGATGAGGCGAAACATCGTGAGGTTA

ATCATACCCTGGGGAATCTGGATCAGGATGAGGATCCGAATCCGTTTGTT

TCCGAGTATAAGGATGTGGGGAGGCCGCATCCTGGGAAGGGGATTGAGCA

TGTGCAGCCGATTGGGTGGGAGAGGAAGGATGTTATTTGAGAGTTGGAGC

GAAGTCTTTTGCTCTTTTCTTGATCGCGATCGATGGCTCTCGACGACTAG

ATGAGGGACTTGAAGTCTTAAACTGCGACCAGGACTGCATAGAGATTACT

ACAGAGAGGCGTTTTGAGGTTTTTGGCGTTGGTTTATAGGTGTGCAAGAT

GGGTTCGGGCGTTTGTTCTGCTTTT
```

This sequence can be found online at world wide web github.com/ash-dieback-crowdsource/data. The sequence of DNA can be found at this position within the open source file: CHAFR746836.1.1_0053300.1 gene=CHAFR746836.1.1_0053300. loc:Cf746836_TGAC_s1v1_scaffold_1027( )115146-117337 segs:1-260,261-620,621-1098 CDS=493-1590 loc: Cf746836_TGAC_s1v1_scaffols_1027|115146-117337|exons:115146-115897,115987-116346,116416-117337 segs:1-752,753-1112,1113-2034.

As represented by the underlined bases shown in SEQ ID No:1, the DNA sequence for *C. fraxinea* encodes an AOX. Accordingly, the AOX inhibitors of the invention, as defined herein, will be effective against this fungus, especially its AOX encoded by SEQ ID No:1.

The agrochemical composition may comprise one or more solvents in which the AOX inhibitor is mixed. The amount of solvents in the composition may range from 1% to 99%, or from 30% to 80%. Suitable solvents include, for example, a non-polar water-immiscible solvent, or a polar aprotic water miscible organic solvent. Non-polar solvents include, for example substituted or unsubstituted aliphatic or aromatic hydrocarbons and esters of plant oils or mixtures thereof. Non-limiting examples of aromatic hydrocarbons include benzene or substituted benzene derivatives such as toluene, xylene, 1,2,4-trimethylbenzene, naphthalene or mixtures thereof. In one embodiment, a solvent includes a mixture of napthalen and 1,2,4-trimethylbenzene. In another embodiment, a solvent is Aromatic 150, a heavy aromatic naptha solvent containing <10% naphthalene and <1.7% 1,2,4-trimethylbenzene.

Alkyl esters can also be used as non-polar, water immiscible solvents. Plant oils may be esterified with various alcohols to form alkyl esters of plant oils. Fatty acids of these plant oils have 5 to 20, or 6 to 15 carbon atoms. Alkyl esters of plant oils include, without limitation, methyl, ethyl and butyl esters of canola (*B. napus*), linseed, safflower (*Carthamus tinctorius* L), soybean and sunflower oils. In one embodiment, the solvent is a mixture of methyl esters. A specific non-limiting example of methyl esters is Agent 2416-21 manufactured by Stepan Company (22 W. Frontage Road, Northfield, Ill.).

Water-miscible polar aprotic solvents can include, for example, alkyl lactates, isopropyl lactate, alkyl carbonates, polyethylene glycols, polyethylene glycol alkyl ethers, polypropylene glycols, and polypropylene glycol alkyl ethers, or mixtures thereof.

The composition may comprise one or more adjuvants. An adjuvant may enhance or improve herbicidal performance, for example. Adjuvants may be added to the composition at the time of formulation, or by the applicator to a mix prior to treatment. Adjuvants include, for example surfactants (emulsifier), crop oil, fertilizers, dispersing agents, compatibility agents, foaming activators, foam suppressants, correctives, and spray colorants (dyes). An adjuvant may be present in any desired amount. For example, a formulation may contain 1% to 3% adjuvant, 3% to 8% of adjuvant, 8% to 16% adjuvant, 17% to 30% adjuvant, or 30% or (e.g. 40% or more) more adjuvant.

The composition may comprise one or more surfactant. A surfactant may increase solubility of the AOX inhibitor in a solution. A surfactant may also affect spray retention, droplet spreading, and dry rates. A surfactant may be anionic or non-ionic. Examples of anionic surfactants include phosphoric mono- and di-esters of long-chain alcohols having 14 to 22 carbon atoms and the salts thereof; phosphoric mono- and di-esters of alkylene oxide addition products of long-chain alcohols having 14 to 22 carbon atoms and the salts thereof; alkylsulphates having 14 to 22 carbon atoms; polyoxyethylene alkyl ether sulphates of alcohols having 14 to 22 carbon atoms; alkane sulphonates having 14 to 22 carbon atoms; and olefin sulphonates having 14 to 22 carbon atoms.

Suitable non-ionic surfactants include, for example, ethoxylated fatty acids, alcohol ethoxylates, tristyrylphenol ethoxylates, ethoxylated sorbitan fatty acid esters or mixtures thereof. Ethoxylated fatty acids include castor or canola oil ethoxylates having at least 25, preferably 27 to 37 ethoxy units, such as Sunaptol® CA350 (castor oil ethoxylate with 35 ethoxy units) of Uniqema (formerly ICI Surfactants), Mergital® EL33 (castor oil ethoxylate with 33 ethoxy units) of Henkel KGaA, Eumulgin® Co3373 (canola oil ethoxylate with 30 ethoxy units) of Henkel KGaA and Ukanil® 2507 (castor oil ethoxylate) of Uniqema.

Surfactants may be present in any desired amount. For example, a surfactant may be present in an amount of about 0.1 to about 30% by weight in the formulation. In a particular embodiment, a surfactant is present in an amount of about 1 to about 9% by weight in the formulation. In another embodiment, a surfactant is present in an amount of about 10 to about 20% by weight in the formulation.

The composition may comprise one or more emulsifier. An emulsifier is a type of surfactant typically used to keep emulsion well-dispersed. Non-limiting examples of the emulsifier include Agent 2201-76, Agent 2416-20, Emulpon CO-360, T-Det C-40®, and Agnique™ SBO-IO. Agent 2201-76 is manufactured by Stepan Company (22 W. Frontage Road, Northfield, Ill.), which is a blend of nonionic and anionic surfactants (82%). The ingredients in Agent 2201-76 are alkylbenzene sulfonate and fatty acid ethoxylate, aromatic petroleum hydrocarbon, i-hexanol and naphthalene. Agent 2416-20 is also manufactured by Stepan Company (22 W. Frontage Road, Northfield, Ill.), which is a blend of nonionic and anionic surfactants (35-37%). Agent 2416-20 also includes aromatic petroleum hydrocarbon (57-58%), and naphthalene (6-7%). Emulpon CO-360 is manufactured by Akzo Nobel Chemicals Ltd. (525 West Van Buren, Chicago, Ill.), which contains ethoxylated castor oil (100% by weight) and oxirane (<0.001% by weight). T-Det C-40® may be purchased from Harcros Organics (5200 Speaker Road., P.O. Box 2930, Kansas City, Kans.), or from Akzo Nobel Chemicals Ltd. (525 West Van Buren, Chicago, Ill.), which is a non-ionic emulsifier, and a brand of ethoxylated (polyethoxylated) castor oil. Agnique™ SBO-IO is manufactured by Cognix GmbH headquartered in Monheim, Germany, which contains alkoxylated triglycerides as an ethoxylated soybean oil.

A crop oil, or a crop oil concentrate, may be used to increase the efficacy of a herbicide formulation. Although not wishing to be bound by any particular theory, a crop oil is believed to keep the leaf surface moist longer than water, which in turn allows more time for the herbicide to penetrate, thereby increasing the amount of herbicide that will enter the plant (e.g. weed). A crop oil can improve uptake of herbicide by plant (e.g. weed). A crop oil can therefore improve, enhance, increase or promote herbicidal efficacy or activity. Crop oils may contain from 1% to 40% by weight, or 1% to 20% by weight in the formulation. A crop oil can be derived from either petroleum oil or vegetable oil. Non-limiting examples of crop oil include soybean oils and petroleum-based oils.

The agrochemical composition of the invention may be in customary formulations. Non-limiting examples include solutions, emulsions, suspensions, wettable powders, powders, dusts, pastes, soluble powders, granules, pellets, emulsifiable concentrate, oil spray, aerosol, natural and synthetic materials impregnated with active compound, and very fine capsules (e.g. in polymeric substances). In certain embodiments, the composition is in a form of an emulsifiable concentrate, wettable powder, granule, dust, oil spray or aerosol.

The composition may optionally include adherent coatings. Such coatings include those that aid the AOX/bc1 inhibitor to adhere to the intended environment, for example, a plant being treated. Adherent coatings include carboxymethylcellulose, natural and synthetic polymers in various forms, such as powders, granules or latexes. Other adherent coatings include gum arabic, polyvinyl alcohol and polyvinyl acetate. Phospholipids, such as cephalins and lecithins, and synthetic phospholipids are also examples of adherent coatings. Further additives may be mineral and vegetable oils.

Colourants can also be included in the compositions. Non-limiting examples are inorganic pigments, such as iron oxide, titanium oxide and Prussian Blue, and organic dye-stuffs, such as alizarin dyestuffs, azo dye-stuffs and metal phthalocyanine dyestuffs, and trace nutrients such as salts of iron, manganese, boron, copper, cobalt, molybdenum and zinc.

The agrochemical compositions according to the invention can be applied in the form of ready mixes. Herbicidal compositions can also be formulated individually and mixed upon use, i.e. applied in the form of tank mixes. The compositions of the invention can be used as such or in the form of their formulations, and furthermore also as mixtures with herbicides, ready mixes or tank mixes. The compositions may also be mixed with other active compounds, such as other fungicides, insecticides, acaricides, nematicides, bird repellents, growth substances, plant nutrients and agents which improve soil structure. For particular application purposes, in particular when applied post-emergence, formulations such as mineral or vegetable oils which are tolerated by plants (for example the commercial product "Oleo DuPont 1 IE") or ammonium salts such as, for example, ammonium sulphate or ammonium thiocyanate, as further additives can be included.

The compositions can be used as such, in the form of their formulations or in the forms prepared therefrom by dilution of a concentrated form, such as ready-to-use or concentrated liquids, solutions, suspensions, emulsions, or solids, such as, powders, pastes, granules and pellets. They are dispersed in the customary manner, for example by watering, spraying, atomizing, dusting or scattering.

The compositions of the invention can be produced by mixing or suspending one or more stabilizers, an active ingredient, and optionally an adjuvant, a diluent or a solvent. In certain embodiments, compositions of the invention can be produced, for example by first mixing or suspending one or more AOX/bc1 inhibitor with a diluent or solvent. Next, the appropriate amount of adjuvant is combined to the resulting mixture containing the AOX/bc1 inhibitor. The AOX/bc1 inhibitor can be added at the end and blended until the formulation becomes mostly or entirely homogeneous.

Plants that may be treated with the agrochemical composition are generally referred to herein as "crop plants". The term "crop plants" as used herein, includes any edible or non-edible plant, including decorative, plant species with commercial value, which is planted and cultivated for commercial use. Thus, crop plants include floral and non-floral plants, trees, vegetable plants, turf, and ground cover. Non-limiting specific examples of crop plants include canola, flax, peas, lentils, beans, linola, mustard, chickpeas, sunflowers, potatoes, seedling alfalfa, onions, soybeans and turf grass. The term "plants" is meant to include germinant seeds, emerging seedlings, and established vegetation, including roots and above-ground portions (for example, leaves, stalks, flowers, fruits, branches, limbs, root, etc.). The term "turf" used herein refers to grass which grow in areas in which they are desired, or purposely planned for and maintained, for example, a lawn. Turf also refers to a sod, where the surface layer of ground consisting of a mat of grass and grass roots.

The application rate of AOX/bc1 inhibitor varies depending, for example, on the crop being treated with the agrochemical composition. In general, the application rate may be from 0.01 kg/ha to 5.00 kg/ha or from 0.03 kg/ha to 3.00 kg/ha of the AOX/bc1 inhibitor.

The inventors have also found that the inhibitors of the invention can be effectively used to treat infections of animal or human pathogens which comprise an AOX enzyme.

In a ninth aspect, there is provided the compound of formula I, which may be alternative oxidase (AOX) inhibitor of the first aspect, for use in therapy or diagnosis.

In a tenth aspect, there is provided the compound of formula I, which may be alternative oxidase (AOX) inhibitor of the first aspect, for use in treating a microbial infection.

In an eleventh aspect, there is provided a method of treating, ameliorating or preventing a microbial infection in a subject, the method comprising, administering to a subject in need of such treatment, a therapeutically effective amount of the compound of formula I, which may be alternative oxidase (AOX) inhibitor of the first aspect.

In a twelfth aspect, there is provided a method of inhibiting activity of a microbial alternative oxidase (AOX) and/or cytochrome $bc_1$ complex, the method comprising contacting a microbial alternative oxidase (AOX) and/or cytochrome $bc_1$ complex with an effective amount of the compound of formula I, which may be alternative oxidase (AOX) inhibitor of the first aspect.

The AOX/bc1 inhibitor may be used to treat a bacterial infection, for example a Gram-positive or a Gram-negative bacterial infection.

Preferably, the AOX/bc1 inhibitor is used to treat a fungal infection. For example, fungi against which the inhibitor is effective may include a filamentous fungus, such as an *Ascomycete*. Examples of fungi against which the inhibitor is effective may be selected from a group of genera consisting of *Aspergillus; Blumeria; Candida; Cryptococcus; Encephalitozoon; Fusarium; Leptosphaeria; Magnaporthe; Phytophthora; Plasmopara; Pneumocystis; Pyricularia; Pythium; Puccinia; Rhizoctonia; richophyton*; and *Ustilago*.

Further examples of fungi may be selected from a group of genera consisting of *Aspergillus* and *Candida*. The fungus may be selected from a group of species consisting of *Aspergillus flavus; Aspergillus fumigatus; Aspergillus nidulans; Aspergillus niger; Aspergillus parasiticus; Aspergillus terreus; Blumeria graminis; Candida albicans; Candida cruzei; Candida glabrata; Candida parapsilosis; Candida tropicalis; Cryptococcus neoformans; Encephalitozoon cuniculi; Fusarium solani; Leptosphaerianodorum; Magnaporthe grisea; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Trichophytoninterdigitale; Trichophyton rubrum*; and *Ustilago maydis*. Further examples of fungi include yeast, such as *Saccharomyces* spp, eg *S. cerevisiae*, or *Candida* spp, and *C. albicans*, which is known to infect humans.

The AOX/bc1 inhibitor may be used to treat a disease associated with human pathogens, such as intestinal disease; Leishmaniasis; Candidiasis; and diseases associated with contact lens usage.

It will be appreciated that *Trypanosoma, Cryptosporidium parvum* and *Blastocystis hominis* can cause intestinal diseases; Leishmaniasis is caused by the *Leishmani* parasite; Candidiasis is caused by *Candida albicans* (commonly known as thrush); and diseases associated with contact lens usage may be caused by the free-living protozoan *Acanthamoeba*.

It will be appreciated that AOX/bc1 inhibitors according to the invention may be used in a medicament, which may be used in a monotherapy, i.e. use of only the AOX/bc1 inhibitor for treating, ameliorating, or preventing a microbial infection. Alternatively, AOX/bc1 inhibitors may be used as an adjunct to, or in combination with, known therapies for treating, ameliorating, or preventing microbial infections, for example known antibacterial agents or antifungal agents.

The AOX/bc1 inhibitors according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising AOX/bc1 inhibitors according to the invention may be used in a number of ways. For instance, oral administration may be required, in which case the inhibitors may be contained within a composition that may, for example, be ingested orally in the form of a tablet, capsule or liquid. Compositions comprising inhibitors of the invention may be administered by inhalation (e.g. intranasally). Compositions may also be formulated for topical use. For instance, gels, creams or ointments may be applied to the skin, for example, adjacent the treatment site.

Inhibitors according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with modulators used according to the invention is required and which would normally require frequent administration (e.g. at least daily injection).

In a preferred embodiment, inhibitors and compositions according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the AOX/bc1 inhibitor that is required is determined by its biological activity and bioavailability, which in turn depends on the mode of administration, the physiochemical properties of the inhibitor and whether it is being used as a monotherapy or in a combined therapy. The frequency of administration will also be influenced by the half-life of the inhibitors within the subject being treated. Optimal dosages to be administered may be determined by those skilled in the art, and will vary with the particular inhibitors in use, the strength of the pharmaceutical composition, the mode of administration, and the advancement of the disease being treated. Additional factors depending on the particular subject being treated will result in a need to adjust dosages, including subject age, weight, gender, diet, and time of administration.

Generally, a daily dose of between 0.01 µg/kg of body weight and 0.5 g/kg of body weight of the inhibitors according to the invention may be used for treating, ameliorating, or preventing the microbial infection, depending upon which inhibitor is used. More preferably, the daily dose of inhibitor is between 0.01 mg/kg of body weight and 500 mg/kg of body weight, more preferably between 0.1 mg/kg and 200 mg/kg body weight, and most preferably between approximately 1 mg/kg and 100 mg/kg body weight.

The inhibitors may be administered before, during or after onset of the microbial infection. Daily doses may be given as a single administration (e.g. a single daily injection). Alternatively, the inhibitors may require administration twice or more times during a day. As an example, inhibitors may be administered as two (or more depending upon the severity of the disease being treated) daily doses of between 25 mg and 7000 mg (i.e. assuming a body weight of 70 kg). A patient receiving treatment may take a first dose upon waking and then a second dose in the evening (if on a two-dose regime) or at 3- or 4-hourly intervals thereafter. Alternatively, a slow release device may be used to provide optimal doses of inhibitors according to the invention to a patient without the need to administer repeated doses.

Known procedures, such as those conventionally employed by the pharmaceutical industry (e.g. in vivo experimentation, clinical trials, etc.), may be used to form specific formulations comprising the inhibitors according to the invention and precise therapeutic regimes (such as daily doses of the inhibitors and the frequency of administration). The inventors believe that they are the first to describe a composition for treating microbial infections, based on the use of the inhibitors of the invention.

Hence, in a thirteenth aspect of the invention, there is provided an antimicrobial composition comprising the compound as represented by formula I, which may be an AOX inhibitor according to the first aspect, and a pharmaceutically acceptable vehicle.

The term "antimicrobial composition" can mean a pharmaceutical formulation used in the therapeutic amelioration, prevention or treatment of any microbial infection, for example a fungal, bacterial or pathogenic infection.

The invention also provides in an fourteenth aspect, a process for making the antimicrobial composition according to the thirteenth aspect, the process comprising contacting a therapeutically effective amount of the compound of formula I, which may be an AOX inhibitor according to the first aspect, and a pharmaceutically acceptable vehicle.

A "subject" may be a vertebrate, mammal, or domestic animal. Hence, inhibitors, compositions and medicaments according to the invention may be used to treat any mammal, for example livestock (e.g. a horse), pets, or may be used in other veterinary applications. Most preferably, however, the subject is a human being.

A "therapeutically effective amount" of the AOX/bc1 inhibitor is any amount which, when administered to a subject, is the amount of medicament or drug that is needed to treat the microbial infection, or produce the desired effect.

For example, the therapeutically effective amount of AOX/bc1 inhibitor used may be from about 0.01 mg to about 800 mg, and preferably from about 0.01 mg to about 500 mg. It is preferred that the amount of inhibitor is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the modulator) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The inhibitor according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The inhibitor may be prepared as a sterile solid composition that may be dissolved or suspended at the time of administration using sterile water, saline, or other appropriate sterile injectable medium.

The inhibitor and pharmaceutical compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The inhibitors according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Embodiments of the invention will now be further described, by way of example only, with reference to the following Examples, and to the accompanying diagrammatic drawings, in which:

FIG. 1 is a schematic drawing showing the mitochondrial respiratory chain, in which I-IV: Respiratory chain complexes; V: ATP synthase; Q: Ubiquinone; $N_{ext/int}$: NADH dehydrogenases; Stb: Strobilurin site of action; SHAM: salicylhydroxamic acid site of action; CN/CO: Cyanide/Carbon monoxide inhibition site; AO: Alternative oxidase; IMS/IM/M: Inter-membrane space/inner membrane/matrix of mitochondria;

Figure 4A:
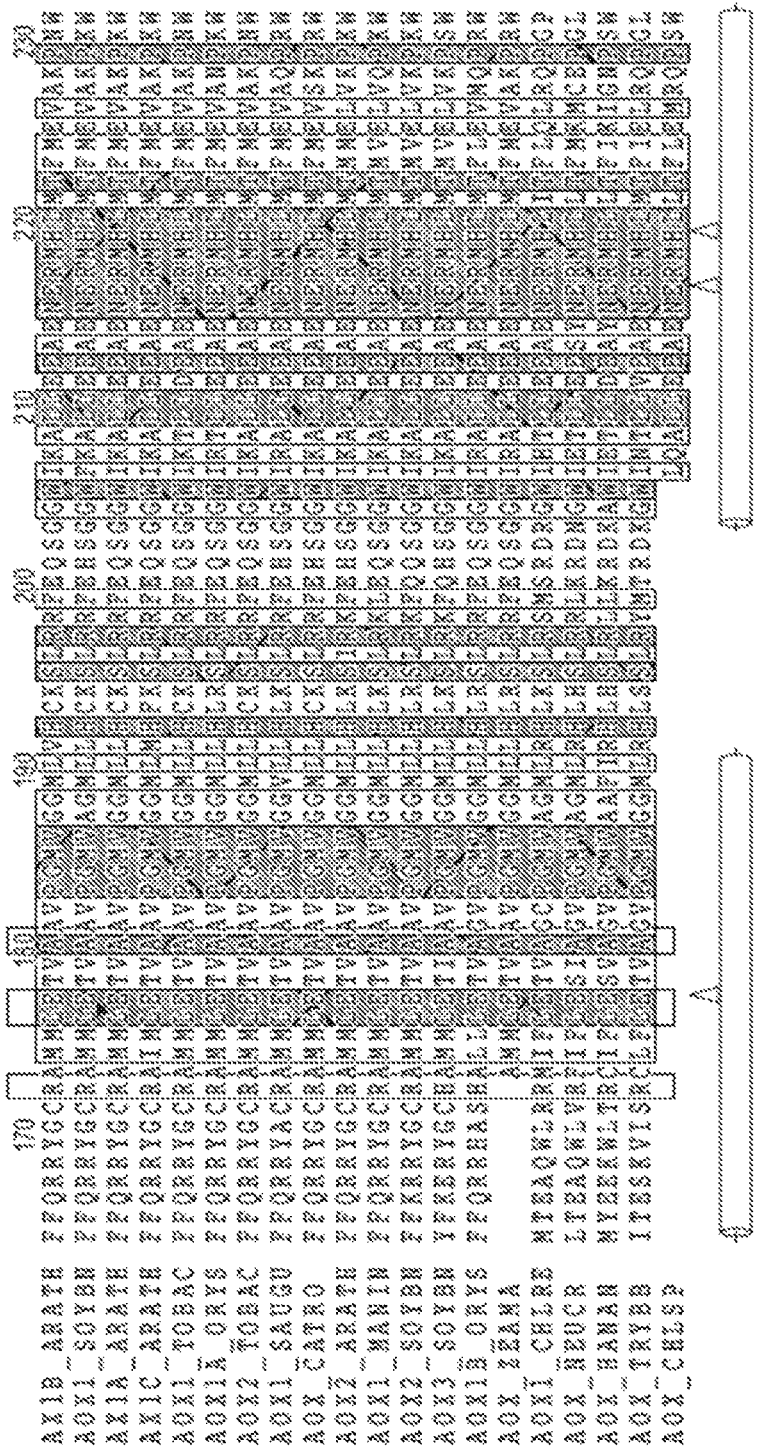
Figure 4B:
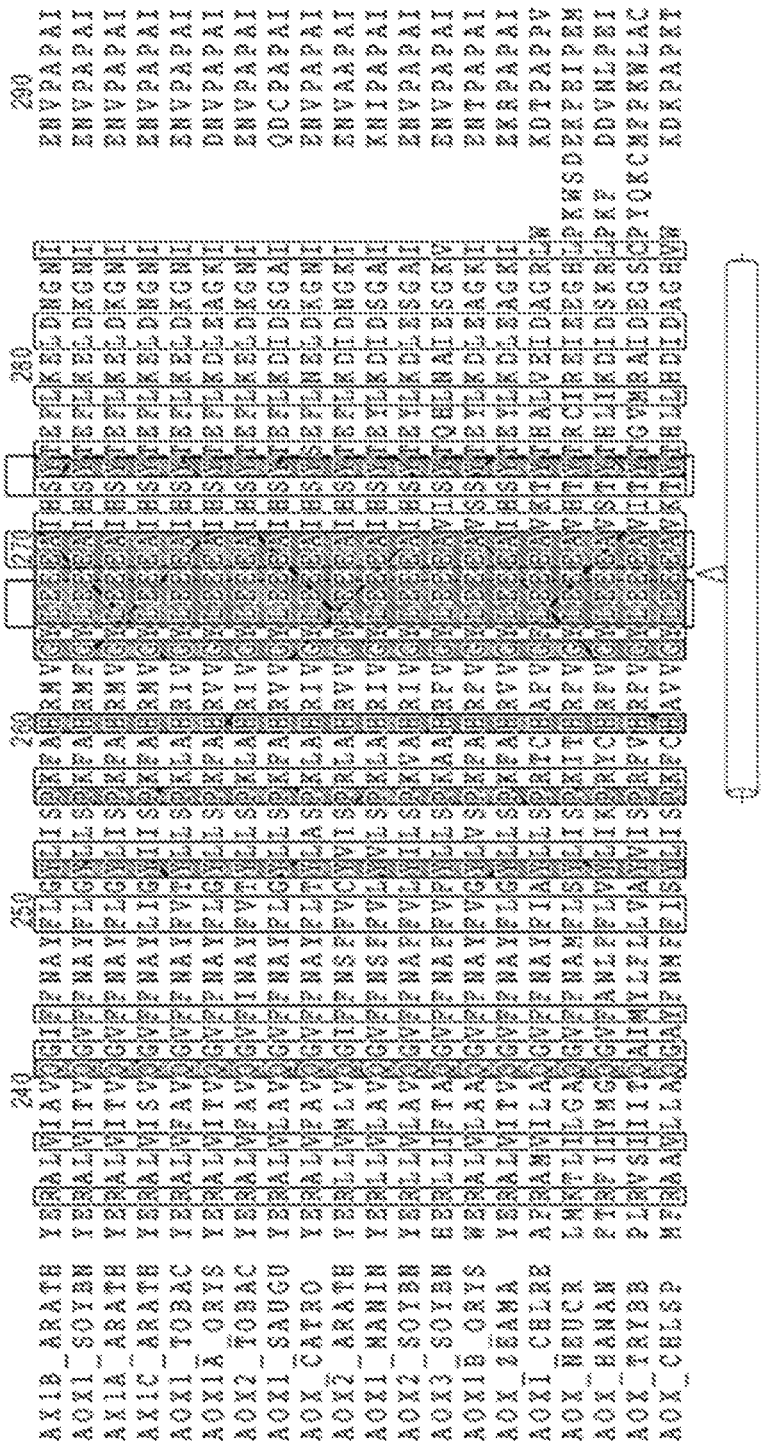
Figure 4C:
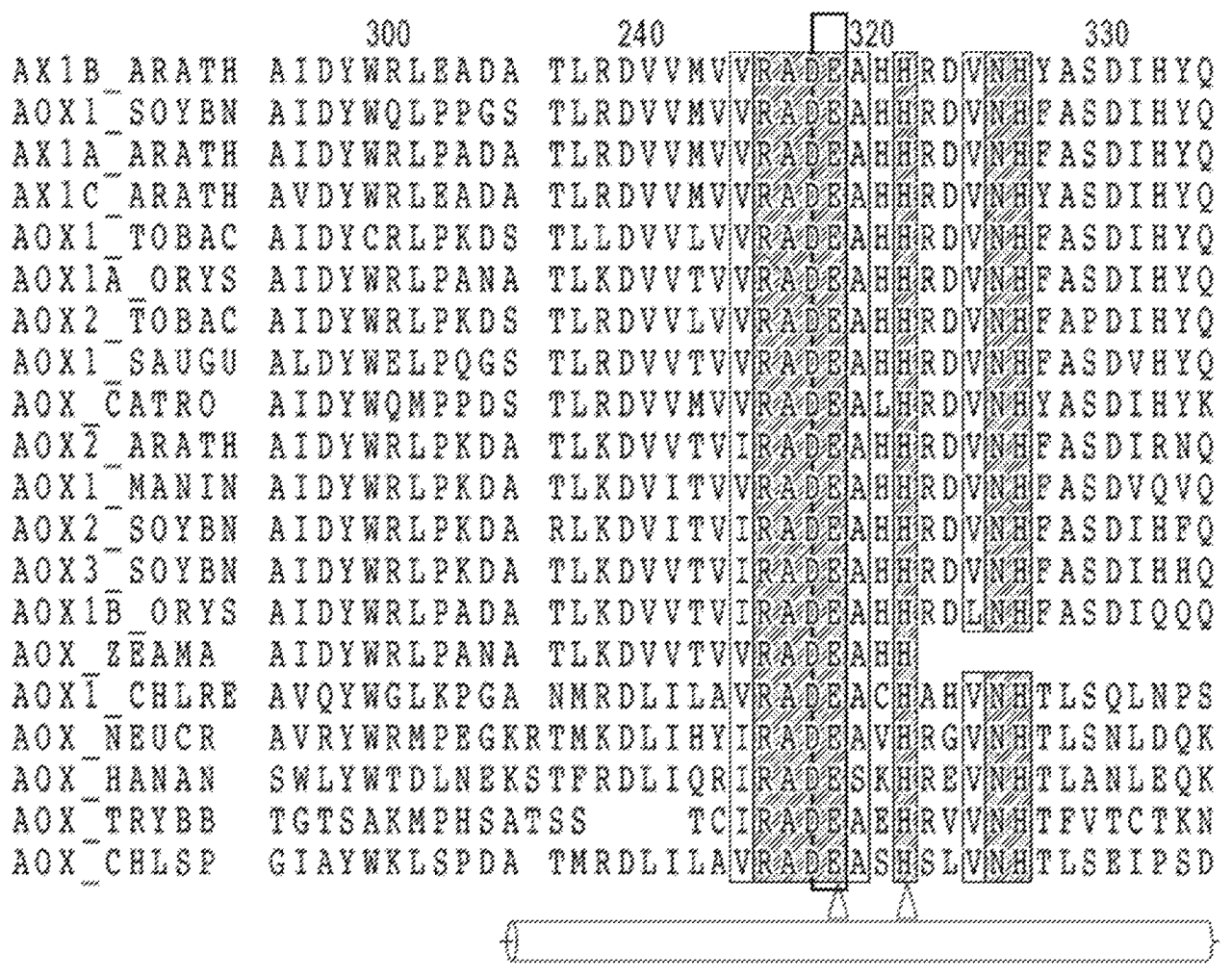
Figure 5:
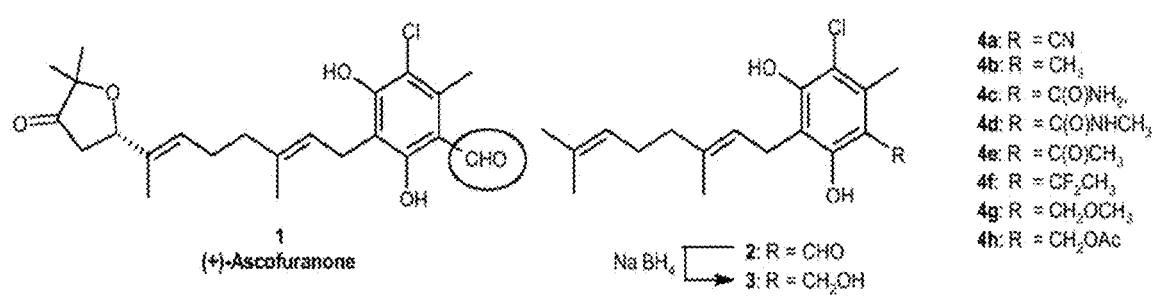
Figure 6:
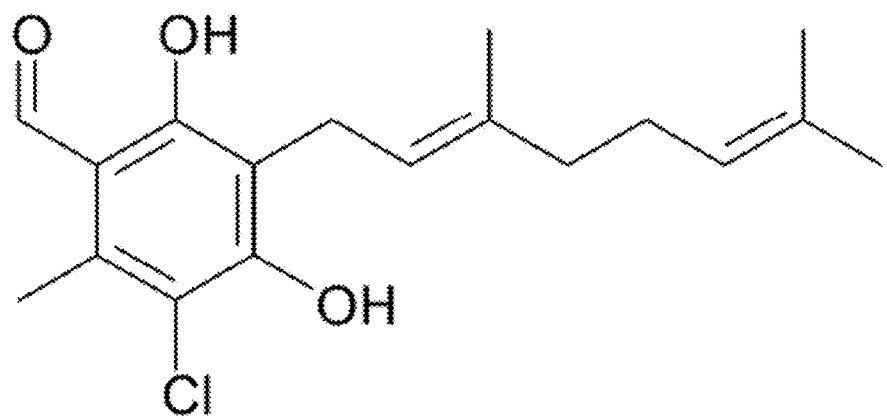
Figure 7:
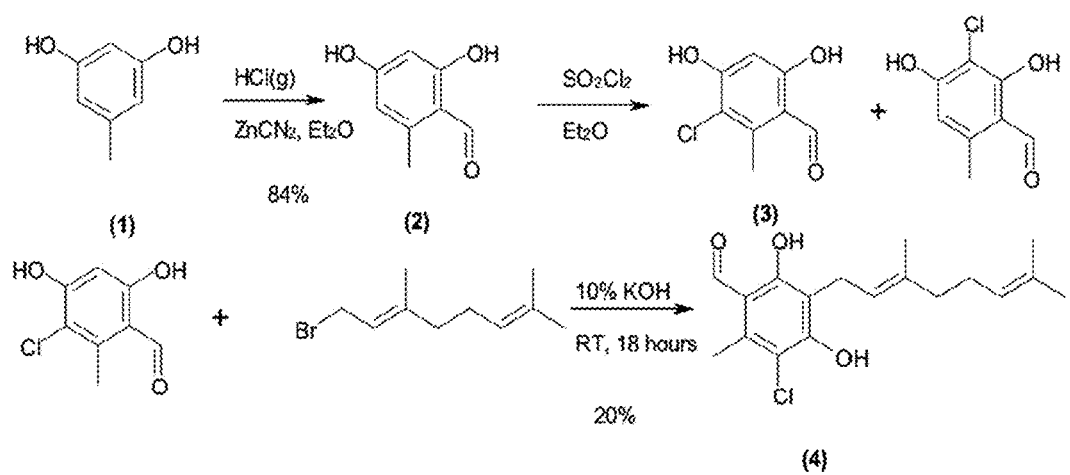
Figure 8:
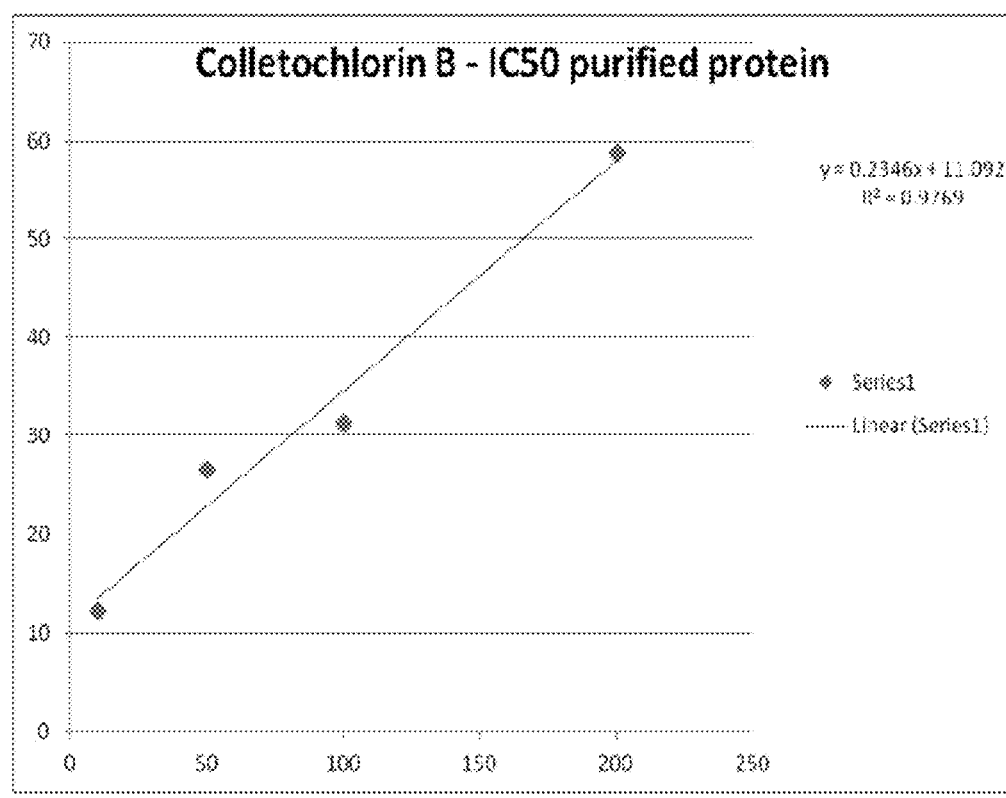

FIGS. 4A-C are a sequence alignment of various alternative oxidases (AOX) of various species showing a consensus sequence. AXIB-ARATH is the AOX enzyme from *Arabidposis thaliana* (SEQ ID No:2), AOX1_SOYBN is the AOX enzyme from soybean (SEQ ID No:3), AOX1_TOBAC is the AOX enzyme from tobacco (SEQ ID No:4), AOX1A_ORYS is the AOX enzyme from *Oryza sativa*-rice (SEQ ID No:5), AOX1_SAUGU is the AOX enzyme from *Sauromatum guttatum* (SEQ ID No:6), AOX_CATRO is the AOX enzyme from *Catharanthus roseus* (SEQ ID No:7), AOX1_MANIN is the AOX enzyme from *Mangifera indica* (SEQ ID No:8), AOX_ZEAMA is the AOX enzyme from Maize (SEQ ID No:9), AOX1_CHLRE is the AOX enzyme from *Chlamydomonas reinhardtii* (SEQ ID No:10), AOX_NEUCR is the AOX enzyme from *Neuropsora crassa* (SEQ ID No:11), AOX_HANAN is the AOX enzyme from *Hansenula anomola* (SEQ ID No:12), AOX_TRYBB is the AOX enzyme from *Trypanosoma brucei* (SEQ ID No:13), and AOX_CHLSP is the AOX enzyme from *Chlamydomonas* species (SEQ ID No:14);

FIG. 5 represents the chemical formula of Ascofuranone (left-hand side) and various embodiments of the AOX inhibitor according to the invention;

FIG. 6 represents the chemical formula of Colletochlorin B;

FIG. 7 shows the chemical synthesis of Colletochlorin B;

FIG. 8 is a graph showing $IC_{50}$ values for Colletochlorin B; and

Figure 9:
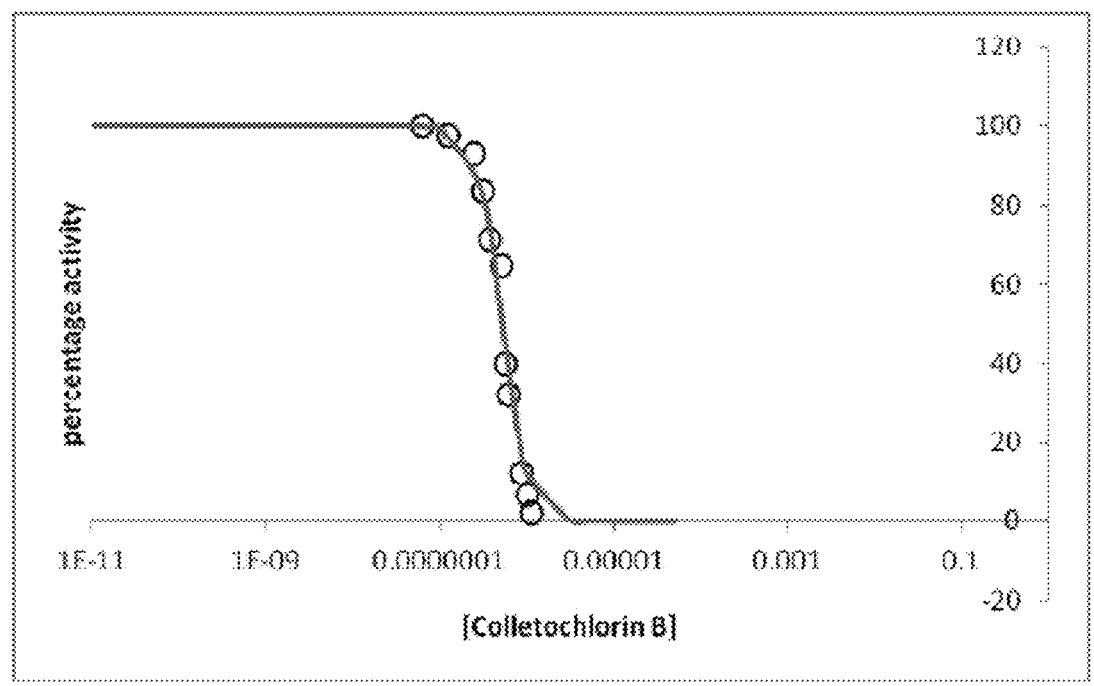

FIG. 9 is a graph showing the effects of Colletochlorin B on cytochrome $bc_1$ activity.

EXAMPLES

Materials & Methods

Figure 3:
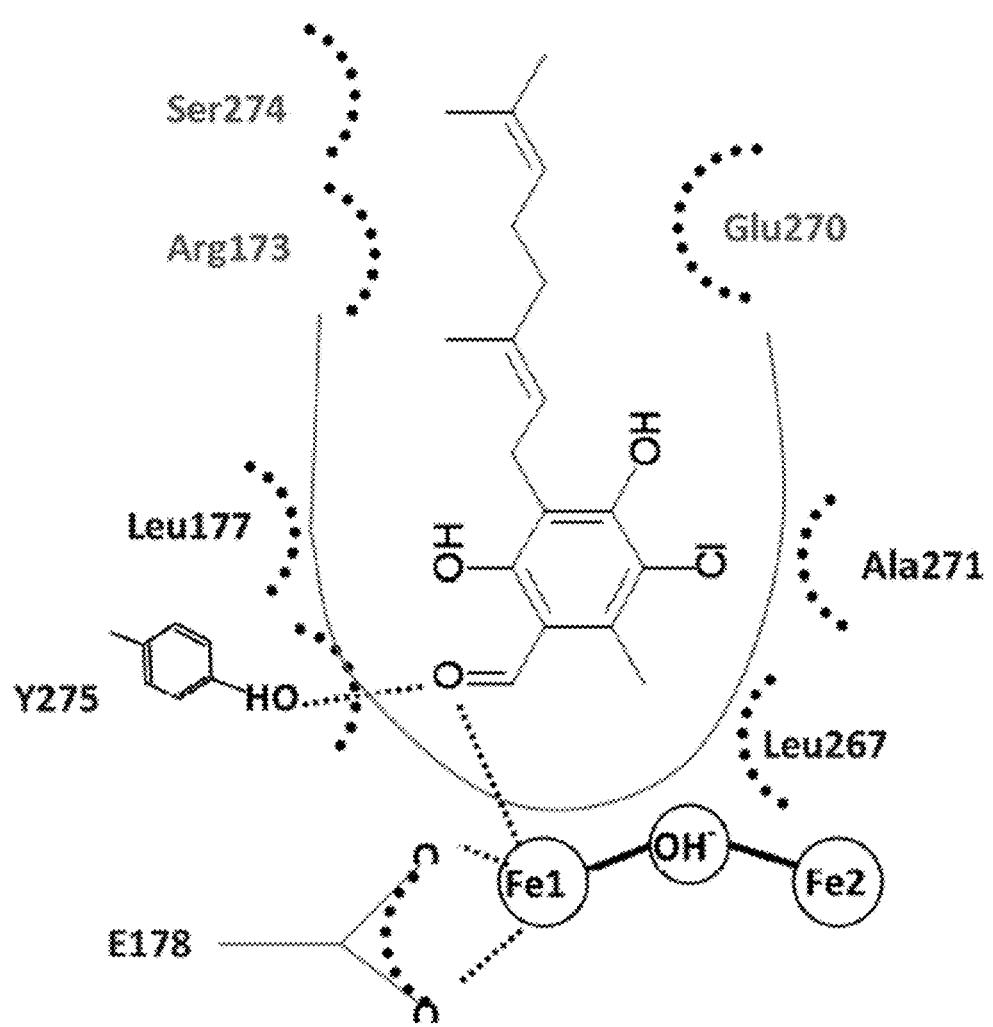
FIG. 3 is a schematic figure showing the hydrophobic pocket and hydrogen-bonding of the inhibitor to the di-iron site of the alternative oxidase (AOX) using *Sauromatum* numbering.

The alternative oxidase (AOX) protein was purified and crystallized according to the techniques outlined in Kido, Y. et al (2010) Biochim. Biophys. Acta 1797, 443-450, and in Kido, Y. et al (2010) Acta. Crystallogr. Sect. F Struct. Biol, Cryst, Commun., 66, 275-278. The crystal structure of the protein was obtained both in the presence and absence of an inhibitor using the vapour hanging-drop technique, as outlined in the papers given above. The inhibitor-binding site was identified from the crystal structure. Analysis of the residues surrounding the pocket revealed that L177, E178, L267, A271 and Y275 shown in FIG. 3 are 100% conserved across all fungal, plant and trypanosomatid species.

Example 1—Characterisation of the Alternative Oxidase (AOX) Binding Pocket

Figure 1:
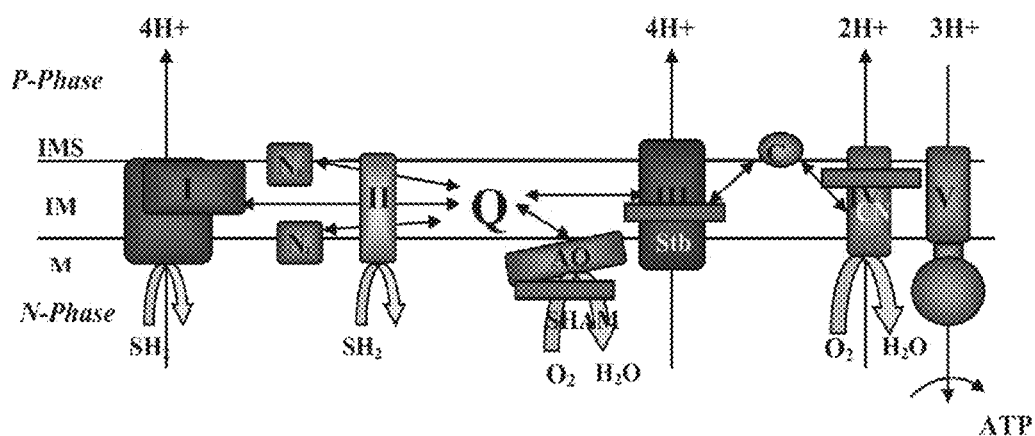
Figure 2:
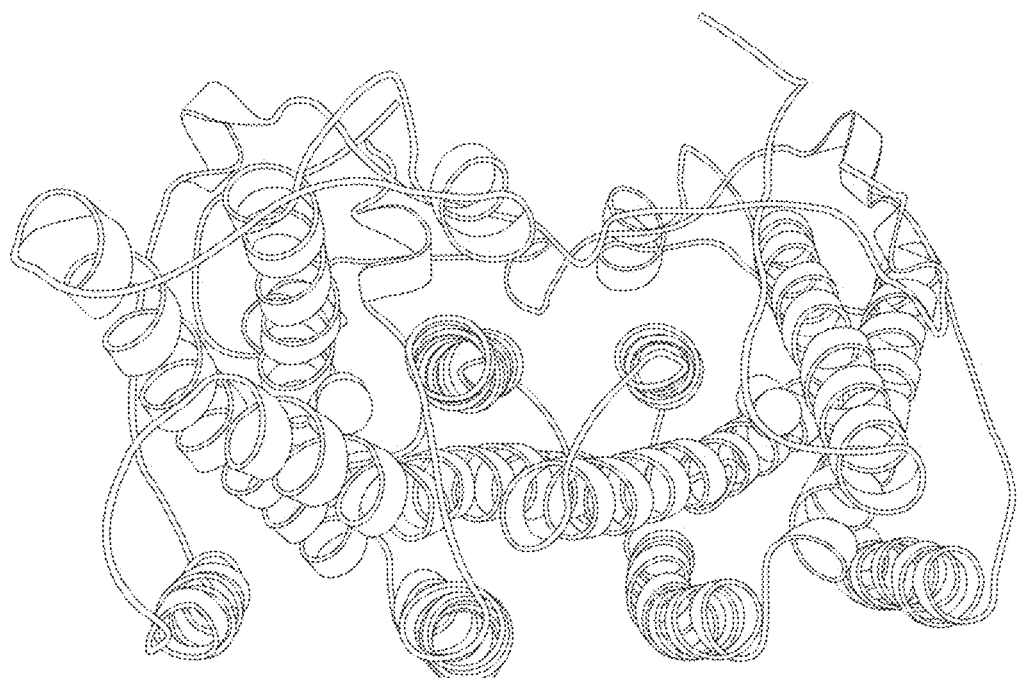
FIG. 2 shows a crystal structure of an alternative oxidase (AOX) protein from *Trypanosoma brucei* in the presence of a stoichiometric inhibitor.

A major breakthrough in this study was the determination of the first ever crystal structure of an alternative oxidase (AOX) protein both in the presence and absence of a stoichiometric inhibitor, as illustrated in FIG. 2. The inventors found that the pocket does not change, i.e. it is substantially the same in the presence or absence of the inhibitor. Knowledge of the crystal structure of AOX in the presence of an inhibitor put the inventors in a very powerful position to undertake some rational fungicidal molecular design, which, as discussed below, has resulted in the production of a library of AOX inhibitor compounds that have the capacity to act as phytopathogenic fungicides specifically targeted at the AOX.

Accordingly, once the inventors had generated the crystal structure of AOX shown in FIG. 2, they went on to characterise the AOX quinone-binding pocket in detail using site-directed mutagenesis. Referring to FIG. 3, there is shown the fully characterised quinone-binding site or pocket of the alternative oxidase enzyme (AOX) of the plant, *Sauromatum guttatum* (Voodoo Lily). The Figure also shows a representative inhibitor (Colletochlorin B) positioned inside the pocket. The six-membered ring of the inhibitor tightly interacts with the hydrophobic residues of the pocket, and the isoprenyl tail of the inhibitor interacts with Arg173, Glu270 and Ser274 residues of the pocket. FIG. 3 also shows that the inhibitor binding pocket (R173, L177, E178, L267, E270, A271, S274 & Y275) is located near the membrane surface, and is within 4 Å of the active-site of the protein. It should be noted that the numbering on FIG. 3 refers to the plant (i.e. *Sauromatum guttatum*) AOX protein, as all AOXs tend to be compared with this protein. The head group aldehyde oxygen is hydrogen-bonded by Glu178 and Tyr275. Although not wishing to be bound by theory, these hydrogen bonds are believed to be important for the potent inhibitory activity of these compounds.

As discussed in the Examples below, the inventors have confirmed that the quinone-binding site of the AOX shown in FIGS. 4A-C is a promising target in the treatment of fungal pathogens. The inventors have prepared a sequence alignment of a number of AOX enzymes, which is shown in FIGS. 4A-C, and it can be seen that the architecture of the AOX binding-site is highly conserved across all AOXs, irrespective of the species from which they are derived. The boxed residues in FIGS. 4A-C represent AOX residues which are involved in inhibitor binding. The Arg173, Glu270 and Ser274 residues shown in FIG. 3 are less conserved. However, as these residues are only involved in the binding of the tail, variation is believed to be less significant with respect to inhibitor sensitivity.

Thus, the detailed knowledge of the nature of the binding site of the AOX of *S. guttatum* is important, as it has revealed that there is a common architecture that can be applied to quinol-binding sites in general, and hence provides further insight into the mechanism of binding. More importantly, this information has assisted in the rational design of phytopathogenic fungicides and human parasites that are specifically targeted to the alternative oxidase.

Based on this information, the inventors set out to design and synthesize a new library of AOX inhibitors, and also to gain further detailed structural knowledge of the nature of the protein-ligand interaction and kinetics. They also tested the extent to which structurally modified inhibitors targeted at the AOX could also inhibit the fungal Qo site, thereby providing a new generation of dual-mode fungicides.

Example 2—Design and Synthesis of AOX Inhibitors

The inventors have designed and synthesised a number of AOX inhibitors based on the compound, ascofuranone, the chemical structures of which are illustrated in FIG. 5. Ascofuranone has a complex synthetic route, and has a reactive aldehyde group (—CHO). Several ascofuranone derivatives were synthesised, namely Colletochlorin B (labelled structure "2" in FIG. 5, where R is CHO), compound "3" shown in FIG. 5, where R is $CH_2OH$, and 4a-4h, where R is as shown in FIG. 5.

The inhibitory effects of some of these compounds were assessed, and the results are summarised in Table 1.

TABLE 1

Inhibitory effects on recombinant AOX protein

| Inhibitor | IC50 |
| --- | --- |
| Ascofuranone | 58 pM |
| Colletochlorin B | 165 pM |
| Octyl Gallate | 105 nM |
| Salicylhydroxamic acid (SHAM) | 7 µM |

Table 1 summarises the concentration of inhibitor required to reduce the respiration of purified recombinant AOX protein by 50%. Respiration was measured as the rate of oxygen consumption in the presence of 1 mM NADH as substrate and the numbers represent the final $I_{50}$ concentration of the inhibitor.

Of the derivatives that were synthesized, Colletochlorin B was one of the most promising candidates, because it has an $IC_{50}$ value of approx 165 pM ($IC_{50}$ for Ascofuranone 58 pM) when tested upon recombinant AOX proteins. This inhibitor was specific for membrane-bound and purified AOX, and did not appear to inhibit other quinol oxidases. Furthermore, Colletochlorin B can also be synthesized by a simple two-step process, which is a significant advantage over ascofuranone.

Example 3—Synthesis of Colletochlorin B

The chemical structure of Colletochlorin B is shown in FIG. 6, and the method used for its synthesis is shown in FIG. 7.

Step 1: Compound (1) to Compound (2)

Orcinol (5 g, 40 mmol) and $Zn(CN)_2$ (7.1 g, 60 mmol) were placed into a 3 necked flask with mechanical stirrer under $N_2$. 50 ml of Ether was added, and the reaction was saturated with HCl gas. After 2 hours, the Ether was decanted off and 50 mls of water added to the reaction mixture. This was heated to 100° C. where the product crashed out of solution. The crude product was collected via buchner filtration, and recrystallised from water to yield the aldehyde (4.6 g) in 76% yield.

Step 2: Compound (2) to Compound (3)

Orcinol Aldehyde (527 mg, 3.5 mmol) was put under $N_2$ and dissolved in anhydrous ether (60 ml) on an ice bath. $SO_2Cl_2$ (1.35 ml, 4.7 mmol) was diluted in ether (15 ml) and then added dropwise over 15 minutes. The reaction was left to stir overnight, and quenched with the addition of water. The Ether layer was washed with 0.1M $NaHCO_3$ and water, then dried over $MgSO_4$ and concentrated under vacuum. The crude solid was then purified via flash chromatography (Toluene: Ethyl acetate 2:1→1:1) to obtain the product (459 mg) in 75% yield.

Step 3: Compound (3) to Compound (4)

3-chloro-4,6-dihydroxy-2-methyl-benzaldehyde (150 mg, 0.8 mmol) was dissolved in 10% KOH (0.9 ml, 0.8 mmol) yielding a deep red solution. The reaction was placed on an ice bath, and geranyl bromide (0.39 ml, 1.6 mmol) was added. The reaction was stirred vigorously overnight, and extracted with ether. The organic layer was washed with $NaHCO_3$ and brine, before being concentrated under vacuum. The resultant oil was purified via flash chromatography (petrol ether 40-60: ether 10:1→3:1) to obtain pure Colletochlorin B (52 mg) in 20% yield.

Example 4—Characterisation of Colletochlorin B

The inventors have confirmed that whilst the hydroxyl groups and the chlorine and methyl substituents on the benzene ring of the inhibitor are believed to be important for high potency, the furanone moiety is redundant as long as a hydrophobic side chain, such as the geranyl group, is retained, as in Colletochlorin B (2).

However, the aldehyde group present in ascofuranone (1) and Colletochlorin (2) is believed to represent a problem for anti-parasitic design for several reasons. Besides their ability to function as hydrogen bond acceptor and to undergo dipole-dipole interaction with AOX, aldehyde groups are chemically reactive enough to undergo reversible covalent modifications and would be generally unsuited to standard pharmaceutical formulations. Furthermore, aldehydes are prone to metabolic oxidation to the respective carboxylic acid with the concomitant non-specific binding to basic transport proteins. Therefore, the inventors set out to remove this aldehyde group using the reducing agent $NaBH_4$, as shown in FIG. 5. Synthesis and analysis of an alcohol-derivative (3) revealed that its inhibitory properties are retained, which is why the various aldehyde bioisosteres, which are represented as compounds 4a-4h in FIG. 5, were produced.

Example 5—Site-Directed Mutagenesis Studies

The inventors have generated mutants of E123 and Y220, and have demonstrated that they are important for enzyme activity and inhibitor-binding.

Site-Directed Mutagenesis and Plasmid Construction

Construction of pREP1-AOX, pREP1-E123A and pREP1-Y220F (used to express wild type AOX and the E123A and Y220F mutants in *S. pombe*) has been described previously [M. S. Albury, C. Affourtit, P. G. Crichton, A. L. Moore, Structure of the plant alternative oxidase—Site-directed mutagenesis provides new information on the active site and membrane topology, J. Biol. Chem. 277 (2002) 1190-1194: M. S. Albury, P. Dudley, F. Z. Watts, A. L. Moore, Targeting the plant alternative oxidase protein to *Schizosaccharomyces pombe* mitochondria confers cyanide-insensitive respiration, J. Biol. Chem. 271 (1996) 17062-17066.]. Mutagenesis of AOX was performed using the Quick Change mutagenesis kit (Stratagene) according to manufacturer's instructions, with plasmid pSLM-AOR [M. S. Albury, C. Affourtit, P. G. Crichton, A. L. Moore, Structure of the plant alternative oxidase—Site-directed mutagenesis provides new information on the active site and membrane topology, J. Biol. Chem. 277 (2002) 1190-1194]. Each full length mutant AOX was excised on a BspHI-BamHI fragment and ligated to the yeast expression vector pREP1/N (a modified version of pREP1 [K. Maundrell, Nmt1 of fission yeast—a highly transcribed gene completely repressed by thiamine, J. Biol. Chem. 265 (1990) 10857-

10864.] in which the NdeI site was replaced with NcoI) which had been digested with NcoI and BamHI, yielding pREP1-E123A and pREP1-Y220F.
Results

TABLE 2

| Condition | Activity (nmol oxygen/min/mg protein | % Inhibition (compared to wt) |
|---|---|---|
| pREP1-AOX—wt | 55 | 0 |
| pREP1-E123A—E123 mutant | 2 | 96 |
| pREP1-Y220F—Y220 mutant | 0 | 100 |

Activity was measured as oxygen consumed/min/mg protein using NADH as substrate when isolated yeast mitochondria (*Schizosaccharomyces pombe*) containing the wild-type and mutant form of the AOX. Note that the inhibitor does not bind to the mutant forms of the oxidase.

Example 6—Effect of Colletochlorin B on Cytochrome $bc_1$ Respiratory Activity

Colletochlorin B and its derivatives have been demonstrated in Examples 1-5 to be a specific inhibitor of the alternative oxidase (AOX) in plants and fungi. Following on from this work, the inventors set out to test whether or not these compounds also have any effect on the respiratory activity of cytochrome $bc_1$ complex. Mitochondria from two sources (rat liver and potato) were titrated with Colletochlorin B (CB), as indicated in typical data summarised in FIG. 9. Both mitochondrial sources did not contain any alternative oxidase (AOX), and so the respiratory activity measured must have been from the cytochrome $bc_1$ complex.

Respiratory activity was measured in a medium containing 0.3M mannitol, 10 mM KCl, 5 mM $MgCl_2$, 1 mM potassium phosphate and 10 mM MOPS (3-(N-morpholino) propanesulfonic acid) buffer pH7.4. Either 0.9 mg of rat liver mitochondria respiring on 5 mM succinate or 0.3 mg potato mitochondria respiring on 1 mM NADH were used. Respiration was measured using a Rank oxygen electrode of 0.4 ml volume at 25° C. in the presence of 1 μM CCCP (Carbonyl cyanide m-chloromethoxy phenylhydrazone). The results were compared with ascochlorin (a known $bc_1$ inhibitor) and azoxystrobin (a commercial fungicide targeted at the $bc_1$ complex).
Results

TABLE 3

| $IC_{50}$ (Rat liver mitochondria) | |
|---|---|
| Compound | $IC_{50}$/nM |
| Ascochlorin | 187 |
| Colletochlorin B | 515 |
| Azoxystrobin | 525 |

TABLE 4

| $IC_{50}$ (Potato mitochondria) | |
|---|---|
| Compound | $IC_{50}$/μM |
| Ascochlorin | 0.5 |
| Colletochlorin B | 0.75 |
| Azoxystrobin | 1.4 |
| Ascofuranone | 30 |

Tables 3 and 4 summarise the concentration of inhibitor that was required to reduce the respiration of cytochrome $bc_1$ complex (in the absence of AOX) by 50%. Respiration was measured as the rate of oxygen consumption in the presence of 1 mM NADH or 5 mM succinate as substrate, and the numbers represent the final $IC_{50}$ concentration of the inhibitor tested. The lower the $IC_{50}$ value the better, since it means that a lower amount of the compound is needed to halve the respiratory activity.

Of the inhibitors that were synthesized, Colletochlorin B was a promising candidate, because it has a lower $IC_{50}$ value (approx 515 nM) than Azoxystrobin (approx 525 nM) when tested on rat liver mitochondria. When tested on potato mitochondria, the $IC_{50}$ value of Colletochlorin B was only 0.75 μM, which was half of the $IC_{50}$ of Azoxystrobin (approx 1.4 μM), and significantly less than the $IC_{50}$ of Ascofuranone (approx 30 μM).

CONCLUSIONS

Careful titration using mitochondria in which the alternative oxidase is absent has surprisingly revealed that the compound is a specific inhibitor of the cytochrome $bc_1$ complex in addition to inhibiting AOX. The data suggest that the compound inhibits the cytochrome $bc_1$ complex at both the Qo and Qi binding-sites of this complex thereby making it a very potent inhibitor of respiration even in the absence of the alternative oxidase. The implications of such a finding suggest that derivatives of this compound would be very specific and potent dual function fungicide, as not only do they inhibit the alternative oxidase (AOX), but also the cytochrome $bc_1$ complex.

It will be appreciated that commercially available fungicides, such as azoxystrobin, against which Colletochlorin B has been tested herein, inhibit only one site (qo) within the bc1 complex. Accordingly, since Colletochlorin B inhibits the cytochrome $bc_1$ complex at both the Qo and Qi binding-sites, and also the AOX, this compound and its derivatives can act as a highly potent and robust inhibitor.

The invention claimed is:

1. A method of treating a fungal infection in a subject, the method comprising administering to a subject in need of such treatment a therapeutically effective amount of the compound of formula I:

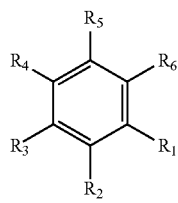

[Formula I]

wherein $R_1$ is a group selected from: CHO; CN; C(O)NH$_2$; C(O)NHCH$_3$; C(O)CH$_3$; COOH; and COOCH$_3$;
$R_2$ is hydrogen, hydroxyl or an alkoxy group with 1 to 3 C atoms;
$R_3$ is a straight chain or branched alkyl or alkylene with 4 to 20 C atoms, that is optionally mono- or polysubstituted by a $C_1$ to $C_4$ alkyl group;
$R_4$ is a hydroxyl group;
$R_5$ is a halogen group; and
$R_6$ is H or a $C_1$ to $C_4$ alkyl group,
wherein the fungal infection is caused by a fungus comprising an alternative oxidase (AOX).

2. The method according to claim 1, wherein $R_2$ is a hydroxyl group.

3. The method according to claim 1, wherein $R_3$ is a straight chain or branched alkyl or alkylene with 6 to 15 C atoms, 8 to 12 C atoms or 8 to 10 C atoms, that is optionally mono- or polysubstituted by a C1 to C4 alkyl group.

4. The method according to claim 1, wherein $R_3$ is a diene having 6 to 15 C atoms that is substituted with at least one methyl group.

5. The method according to claim 1, wherein $R_5$ is a chlorine, bromine, fluorine or iodine group.

6. The method according claim 1, wherein $R_5$ is a chlorine group; or wherein R6 is a methyl, ethyl or propyl group.

7. The method according claim 1, wherein:
$R_1$ is selected from CHO; CN; C(O)NH$_2$; C(O)NHCH$_3$; C(O)CH$_3$; COOH; and COOCH$_3$;
$R_2$ is a hydroxyl group;
$R_3$ is a straight chain or branched alkyl or alkylene with 4 to 20 C atoms, that is optionally mono- or polysubstituted by a $C_1$ to $C_4$ alkyl group;
$R_4$ is a hydroxyl group;
$R_5$ is a chlorine atom; and
$R_6$ is H or a $C_1$ to $C_4$ alkyl group.

8. The method according to claim 1, wherein:
$R_1$ is selected from CHO; CN; C(O)NH$_2$; C(O)NHCH$_3$; C(O)CH$_3$; COOH; and COOCH$_3$;
$R_2$ is a hydroxyl group;
$R_3$ is a straight chain or branched alkyl or alkylene with 6 to 15 C atoms, that is optionally mono- or polysubstituted by a $C_1$ to $C_2$ alkyl group;
$R_4$ is a hydroxyl group;
$R_5$ is a chlorine atom; and
$R_6$ is H or a $C_1$ to $C_4$ alkyl group.

9. The method according to claim 1, wherein:
$R_1$ is selected from CHO; CN; C(O)NH$_2$; C(O)NHCH$_3$; C(O)CH$_3$; COOH; and COOCH$_3$;
$R_2$ is a hydroxyl group;
$R_3$ is an alkylene chain having 8 to 10 C atoms, and is substituted with at least one methyl group;
$R_4$ is a hydroxyl group;
$R_5$ is a chlorine atom; and
$R_6$ is a methyl group.

10. The method of claim 1, wherein the subject is human.

11. The method of claim 1, wherein the fungus is selected from a group of genera consisting of *Aspergillus; Blumeria; Candida; Cryptococcus; Encephalitozoon; Fusarium; Leptosphaeria; Magnaporthe; Phytophthora; Plasmopara; Pneumocystis; Pyricularia; Pythium; Puccinia; Rhizoctonia; Trichophyton;* and *Ustilago.*

12. The method of claim 11, wherein the fungus is selected from a group of species consisting of *Aspergillus flavus; Aspergillus fumigatus; Aspergillus nidulans; Aspergillus niger; Aspergillus parasiticus; Aspergillus terreus; Blumeria graminis; Candida albicans; Candida cruzei; Candida glabrata; Candida parapsilosis; Candida tropicalis; Cryptococcus neoformans; Encephalitozoon cuniculi; Fusarium solani; Leptosphaerianodorum; Magnaporthe grisea; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Trichophytoninterdigitale; Trichophyton rubrum;* and *Ustilago maydis.*

13. The method of claim 1, wherein the fungus is *Saccharomyces* spp., *S. cerevisiae; Candida* spp., or *C. albicans.*

* * * * *

UNITED STATES PATENT AND TRADEMARK OFFICE
CERTIFICATE OF CORRECTION

PATENT NO. : 11,565,996 B2
APPLICATION NO. : 17/060013
DATED : January 31, 2023
INVENTOR(S) : Anthony Lennox Moore et al.

It is certified that error appears in the above-identified patent and that said Letters Patent is hereby corrected as shown below:

In the Claims

In Column 45, Line 33, Claim 3, delete "C1 to C4" and insert -- $C_1$ to $C_4$ --, therefor.

In Column 45, Line 39, Claim 6, delete "according claim" and insert -- according to claim --, therefor.

In Column 45, Line 41, Claim 7, delete "according claim" and insert -- according to claim --, therefor.

Signed and Sealed this
Twelfth Day of September, 2023

Katherine Kelly Vidal
*Director of the United States Patent and Trademark Office*